US009211340B2

(12) United States Patent
Botti

(10) Patent No.: US 9,211,340 B2
(45) Date of Patent: Dec. 15, 2015

(54) MEANS AND METHODS OF ENHANCING DELIVERY TO BIOLOGICAL SYSTEMS

(76) Inventor: Paolo Botti, Vessy (CH)

( * ) Notice: Subject to any disclaimer, the term of this patent is extended or adjusted under 35 U.S.C. 154(b) by 995 days.

(21) Appl. No.: 12/443,236

(22) PCT Filed: Sep. 26, 2007

(86) PCT No.: PCT/EP2007/008396

§ 371 (c)(1), (2), (4) Date: Nov. 12, 2009

(87) PCT Pub. No.: WO2008/037463

PCT Pub. Date: Apr. 3, 2008

(65) Prior Publication Data

US 2010/0062050 A1 Mar. 11, 2010

(30) Foreign Application Priority Data

Sep. 27, 2006 (EP) .................................... 06020286
Jul. 5, 2007 (EP) .................................... 07013218

(51) Int. Cl.
*A61K 47/48* (2006.01)

(52) U.S. Cl.
CPC ..... *A61K 47/48038* (2013.01); *A61K 47/48046* (2013.01); *A61K 47/48215* (2013.01)

(58) Field of Classification Search
CPC .................. A61K 47/48038; A61K 47/48046; A61K 47/48215
USPC ...... 536/23.1, 24.5; 514/44 A, 44 R; 562/560
See application file for complete search history.

(56) References Cited

U.S. PATENT DOCUMENTS 6,657,052 B1 * 12/2003 Turnbull ...................... 536/23.1
6,914,148 B2 * 7/2005 Manoharan et al. ............ 558/70
2003/0185788 A1 * 10/2003 Rothbard et al. .......... 424/78.22

FOREIGN PATENT DOCUMENTS

| | | | |
|---|---|---|---|
| EP | 0 846 680 | A1 | 6/1998 |
| JP | 2002-502376 | A | 1/2002 |
| JP | 2005-538035 | A | 12/2005 |
| WO | 97/42819 | A1 | 11/1997 |
| WO | 98/52614 | A2 | 11/1998 |
| WO | 02/065986 | A2 | 8/2002 |
| WO | 02/065986 | A3 | 8/2002 |
| WO | 02/069930 | A1 | 9/2002 |
| WO | 03/101402 | A2 | 12/2003 |
| WO | 2005/085159 | A1 | 9/2005 |

OTHER PUBLICATIONS

Michel et al. Tetrahedron Letters 44 (2003) 6579-6582.*

Ekelund, S., et al., Guanidino-Containing Drugs in Cancer Chemotherapy: Biochemical and Clinical Pharmacology, Biochemical Pharmacology, 2001, 61(10), 1183-1193.

Funhoff, A., et al., Poly(3-Guanidinopropyl Methacrylate): A Novel Cationic Polymer for Gene Delivery, Bioconjugate Chemistry, 2004, 15(23), 1212-1220.

Linkletter, B.A., et al., Solid-Phase Synthesis of Oligopurine Deoxynucleic Guanidine (DNG) and Analysis of Binding with DNA Oligomers, Nucleic Acids Research, 2001, 29(11), 2370-2376.

Litovchick, A., et al., Aminoglycoside-Arginine Conjugates that Bind TAR RNA: Synthesis, Characterization, and Antiviral Activity, Biochemistry, 2000, 39(11), 2828-2852.

Pei-Sze NG, Part One: Synthesis and Applications of Endcapped Oligonucleotides. PTwo: Synthesis and Cellular Delivery of Amine and Guanidinium Functionalized Gold Nanoparticles, Dissertation, May 1, 2004, pp. 1-170, Purdue University.

Prakash, T., et al., 2'-O-[Guanidinium)ethyl]-Modified Oligonucleotides: Stabilizing Effect on Duplex and Triplex Structures, Organic Letters, 2004, 6(12), 1971-1974.

Sen, J., et al., Design, Syntheses, and Transfection Biology of Novel Non-cholesterol-Based Guanidinylated Cationic Lipids, J. Med. Chem. 2005, 48, 812-820.

Traber, R., et al., Isolierung und Struckterermittlung der neuen Cyclosporine E, F, G, H und I, Helvetica Chimica Acta, 1982, 65(5), 1655-1677.

Zhang, et al., Guanidinylated Allylamine-N-Isopropylacrylamide Copolymer Nonviral Transgene Vectors, International Journal of Pharmaceutics, 2007, 331(1), 116-122.

Zhou, P., et al., Novel Binding and Efficient Cellular Uptake of Guanidine-Based Peptide Nucleic Acids, Journal of the American Chemical Society, 2003, 125(23), 6878-6879.

* cited by examiner

*Primary Examiner* — Janet Epps-Smith
(74) *Attorney, Agent, or Firm* — Pillsbury Winthrop Shaw Pittman LLP

(57) ABSTRACT

This invention relates to a peptide or polypeptide (a) which is esterified or thio-esterified (i) at the carboxylate of the C-terminus with a guanidinium alkanol, a guanidinium alkanethiol, a PEG substituted with a guanidinium group and having a free hydroxyl group, or a PEG substituted with a guanidinium group and a sulfhydryl group; (ii) at a side-chain carboxylate of one or more Asp or Glu residues, if present, with a guanidinium alkanol, a guanidinium alkanethiol, a PEG substituted with a guanidinium group and having a free hydroxyl group, or a PEG substituted with a guanidinium group and a sulfhydryl group; (iii) at a hydroxyl group of one or more Ser, Thr or Tyr residues, if present, with a guanidinium alkanoic acid or a PEG substituted with a guanidinium group and a carboxyl group; (iv) at a sulfhydryl group of one or more Cys residues, if present, with a guanidinium alkanoic acid or a PEG substituted with a guanidinium group and a carboxyl group; and/or (v) at the N-terminus with a guanidinium alkanoic acid or a PEG substituted with a guanidinium group and a carboxyl group, wherein said N-terminus is previously amidated with an alpha- or beta-hydroxy acid, and wherein the ester is formed between the hydroxy group of said alpha- or beta-hydroxy acid and the carboxylic group of said guanidinium alkanoic acid or said PEG substituted with a guanidinium group and a carboxyl group; and/or (b) which contains one or more disulfides, the disulfide being formed between the sulfhydryl group of a Cys reside, if present, and a guanidinium alkanethiol or a PEG substituted with a guanidinium group and a sulfhydryl group.

13 Claims, 9 Drawing Sheets

Figure 1:
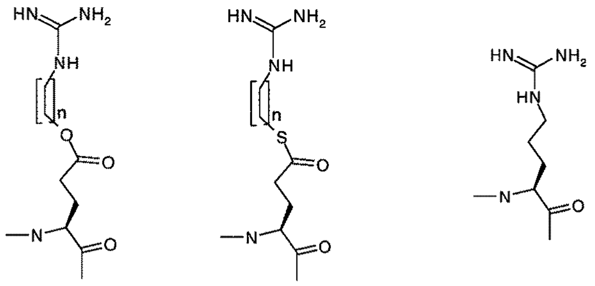

Column MN 250x4 Nucleosil, 300, 7 C8. SN: 4100021, batch: 25500032, cat. number: 720063-40. A: 100%H20, 0.1%TFA, B: 90%CH3CN, 10%H2O, 0.1%TFA.
Quantity injected: unknown.

SampleName Imhof final HPLC bis; Vial 3; Injection 1; Channel W2996 ; Date Acquired 25.04.2006 20:12:40

Peak Results

| | Name | RT | Area | % Area |
|---|---|---|---|---|
| 1 | | 27.921 | 5846531 | 100.00 |

MEANS AND METHODS OF ENHANCING DELIVERY TO BIOLOGICAL SYSTEMS

RELATED APPLICATIONS

This application is the National Phase of International Application PCT/EP2007/008396 filed Sep. 26, 2007 which designated the U.S. and that International Application was published under PCT Article 21(2) in English, and claims priority to European Application Serial No. 06020286.8, filed Sep. 27, 2006 and European Application Serial No. 07013218.8, filed Jul. 5, 2007, all of which applications are incorporated herein by reference in their entirety.

This invention relates to a peptide or polypeptide (a) which is esterified or thio-esterified (i) at the carboxylate of the C-terminus with a guanidinium alkanol, a guanidinium alkanethiol, a PEG substituted with a guanidinium group and having a free hydroxyl group, or a PEG substituted with a guanidinium group and a sulfhydryl group; (ii) at a side-chain carboxylate of one or more Asp or Glu residues, if present, with a guanidinium alkanol, a guanidinium alkanethiol, a PEG substituted with a guanidinium group and having a free hydroxyl group, or a PEG substituted with a guanidinium group and a sulfhydryl group; (iii) at a hydroxyl group of one or more Ser, Thr or Tyr residues, if present, with a guanidinium alkanoic acid or a PEG substituted with a guanidinium group and a carboxyl group; (iv) at a sulfhydryl group of one or more Cys residues, if present, with a guanidinium alkanoic acid or a PEG substituted with a guanidinium group and a carboxyl group; and/or (v) at the N-terminus with a guanidinium alkanoic acid or a PEG substituted with a guanidinium group and a carboxyl group, wherein said N-terminus is previously amidated with an alpha- or beta-hydroxy acid, and wherein the ester is formed between the hydroxy group of said alpha- or beta-hydroxy acid and the carboxylic group of said guanidinium alkanoic acid or said PEG substituted with a guanidinium group and a carboxyl group; and/or (b) which contains one or more disulfides, the disulfide being formed between the sulfhydryl group of a Cys reside, if present, and a guanidinium alkanethiol or a PEG substituted with a guanidinium group and a sulfhydryl group.

In the specification, a number of documents including patent applications and manufacturers' manuals is cited. The disclosure of these documents, while not considered relevant for the patentability of this invention, is herewith incorporated by reference in its entirety.

An increasing number of pharmaceutically active agents is of peptidic or proteinaceous nature or comprises nucleic acids. Administration of such drugs in many cases can only be effected in an invasive manner. However, invasive administration frequently can only be performed by medical staff or is at least cumbersome for the patient. Furthermore, intravenous administration often entails significant degradation of the drug in the liver. However, non-invasive administration is unfortunately not available for the majority of the above-mentioned drugs since they carry electrostatic charges. The presence of electrostatic charges, in particular negative charges, generally renders cell membranes an insurmountable barrier for such pharmaceutically active agents.

There is a group of peptides also referred to as membrane-penetrating peptides including the Antennapedia peptide (see, for example, Zorco and Langel, Advanced Drug Delivery Reviews, 57, 529-545 (2005). These membrane-penetrating peptides are able to efficiently cross the plasma membrane of cells, either alone or linked to protein "cargo". Membrane-penetrating peptides are generally amphipathic and carry a number of positive charges at physiological pH. In fact, one of the most efficient cell-penetrating peptides is simply polyarginine. The mechanism of cell import is likely a consequence of the charge state since so far no difference has been reported between D- and L-peptides.

Poduslo et al. (Biochemistry 43, 6064-6075 (2004)) describe design and chemical synthesis of a magnetic resonance contrast agent with high blood brain barrier permeability. This contrast agent is a derivatized amyloid-β peptide. Derivatization includes substitution of Asp and Glu residues with asparagyl/glutamyl-4-aminobutane residues. In other words, the carboxylates of aspartate and glutamate form amide bonds with 1,4-diamino-butane. It is considered that these modifications render the derivatized peptide capable to cross the blood brain barrier.

Vigneron et al. (Proc. Natl. Acad. Sci. USA 93, 9682-9686 (1996)) describe guanidinium-cholesterol cationic lipids as constituents of micelles and liposomes, wherein polynucleotides which are to be transfected are present in the lumen of the micelles or liposomes. It is reported that the guanidinium group appears particularly well-suited for interaction with the phosphate residues of polynucleotides with which it is able to establish a pair of hydrogen bonds. As a consequence, spontaneous formation of DNA/lipid aggregates is facilitated or enabled.

Prokai et al. (Med. Res. Rev. 20, 367-416 (2000)) describe chemical delivery systems based on the redox conversion of a lipophilic dihydropyridine into a ionic, lipid-insoluble pyridinium salt. Since the redox potentials of blood and brain, respectively, are such that oxidation occurs in the brain but not in the blood, it follows that the oxidized form is trapped in the central nervous system. As a consequence, efficient translocation of a drug operably linked to such chemical delivery system across the blood brain barrier is observed.

However, the prior art fails to provide simple, reversible and non-immunogenic means of enhancing the capability of proteins, nucleic acids, liposomes or micelles to cross membranous barriers in the human or animal body.

In view of these limitations, the technical problem underlying the present invention was therefore the provision of improved or alternative means and methods for the modification of the pharmacological properties of pharmaceutically active agents.

Accordingly, this invention relates to a peptide or polypeptide (a) which is esterified or thio-esterified (i) at the carboxylate of the C-terminus with a guanidinium alkanol, a guanidinium alkanethiol, a PEG substituted with a guanidinium group and having a free hydroxyl group, or a PEG substituted with a guanidinium group and a sulfhydryl group; (ii) at a side-chain carboxylate of one or more Asp or Glu residues, if present, with a guanidinium alkanol, a guanidinium alkanethiol, a PEG substituted with a guanidinium group and having a free hydroxyl group, or a PEG substituted with a guanidinium group and a sulfhydryl group; (iii) at a hydroxyl group of one or more Ser, Thr or Tyr residues, if present, with a guanidinium alkanoic acid or a PEG substituted with a guanidinium group and a carboxyl group; (iv) at a sulfhydryl group of one or more Cys residues, if present, with a guanidinium alkanoic acid or a PEG substituted with a guanidinium group and a carboxyl group; and/or (v) at the N-terminus with a guanidinium alkanoic acid or a PEG substituted with a guanidinium group and a carboxyl group, wherein said N-terminus is previously amidated with an alpha- or beta-hydroxy acid, and wherein the ester is formed between the hydroxy group of said alpha- or beta-hydroxy acid and the carboxylic group of said guanidinium alkanoic acid or said PEG substituted with a guanidinium group and a carboxyl group; and/or (b) which contains one or more disulfides, the disulfide being formed between the sulfhydryl group of a Cys reside, if present, and a guanidinium alkanethiol or a PEG substituted with a guanidinium group and a sulfhydryl group.

The term "peptide" as used herein refers to condensation polymers of amino acids which consist of up to 30 amino acids. The term "polypeptide" as used herein refers to condensation polymers or more than 30 amino acids. It is understood that the term "polypeptide" comprises proteins. Preferred polypeptides are proteins. The terms "peptide" and "polypeptide" furthermore both comprise fragments of proteins and synthetic molecules. Furthermore, antibodies as well as fragments and derivatives thereof are, depending on their size, comprised by either of the terms. Preferably, a peptide or polypeptide according to the invention differs from a corresponding naturally occurring peptide or polypeptide or from a peptide or polypeptide the pharmacological properties of which are to be improved only in that it is esterified and/or thioesterified according to (a) and/or it contains one or more disulfide according to (b).

The terms "esterified" and "thioesterified" refer to the presence of one or more ester functional groups —C(═O)O— or thioester functional groups —C(═S)O—, wherein the acid, alcohol or thiol component of the ester or thioester is provided by the peptide or polypeptide in its form prior to esterification or thioesterification. The same applies to the disulfide according to (b) in that one of the sulfur atoms of the disulfide is provided by the sulfhydryl group of a Cys residue of said peptide or polypeptide. In other words, the terms "esterified", "thio-esterified" and "disulfide being formed" provide a structural characterization of the peptide or polypeptide according to the invention in terms of its constituent moieties, namely a peptide or polypeptide which is not esterified or thio-esterified according to (a) and does not contain one or more disulfides according to (b), preferably a naturally occurring peptide or polypeptide on the one side, and said guanidinium alkanol, guanidinium alkanethiol or guanidinium alkanoic acid on the other side.

The peptides and polypeptides of the invention are defined in terms of the constituent moieties, i.e., a peptide or polypeptide which is occurring in nature of a peptide or polypeptide the pharmacological properties of which are to be improved on the one side and the guanidinium group-containing compounds (guanidinium alkanols, guanidinium alkanthiols, guanidinium alkanoic acids etc.) defined herein on the other side. These constituent moieties are covalently linked to each other in the peptides and polypeptides of the invention by ester, thioester and/or disulfide bonds. Exemplary peptides/polypeptides are shown in the Examples and Figures enclosed herewith.

A guanidinium alkanol according to the invention is an alkane carrying a guanidinium group —NH—C(═NH)—$NH_2$ and a hydroxyl group. In one preferred embodiment, no further functional groups are present. Also preferred are ω-guanidinium alkan-1-ols. The same applies mutatis mutandis to guanidinium alkanethiols and guanidinium alkanoic acids according to the invention. Accordingly, a guanidinium alkanoic acid is an alkane carrying a carboxyl group and a guanidinium group. Preferred are ω-guanidinium alkan-1-oic acids.

As described above, a PEG chain $—CH_2CH_2(OCH_2CH_2)_k—$ may take the place of the above described alkane in one or more occurrences of said guanidinium alkanols, guanidinium alkanethiols and/or guanidinium alkanoic acids, thereby giving rise to said PEG substituted with a guanidinium group and having a free hydroxyl group, said a PEG substituted with a guanidinium group and a sulfhydryl group or said a PEG substituted with a guanidinium group and a carboxyl group. Replacing the alkane moiety with PEG is a means of reducing side effects, it any, of a treatment with peptides or polypeptides of the invention.

Embodiment (v) opens a route for introducing a guanidinium group or a further guanidinium group in case none of the options (i) to (iv) is available or these options are already exhausted. Preferred alpha-hydroxy acids are glycolic acid (2-hydroxyethanoic acid) and lactic acid (2-hydroxypropanoic acid). A preferred beta-hydroxy acid is 3-hydroxypropanoic acid.

Figure 2:
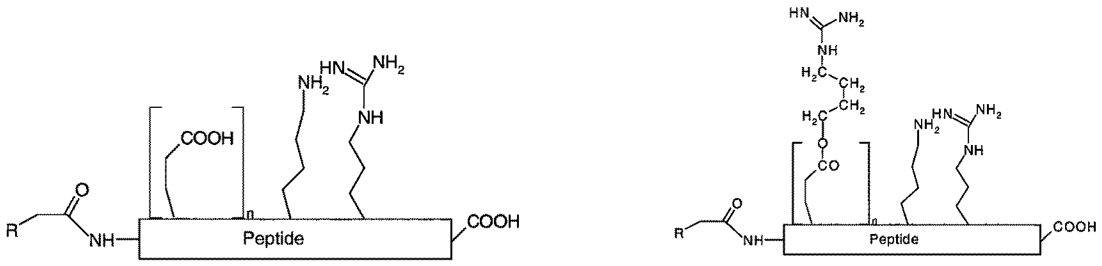

Exemplary embodiments are shown in FIGS. 1 and 2.

The introduction of one or more guanidinium groups in a peptide or polypeptide significantly enhances the capability of said peptide or polypeptide to cross a biological membrane (cf. the examples enclosed herewith). Embodiments (i) and (ii) are particularly advantageous since concomitant with the introduction of a guanidinium group a negative charge of a carboxylate—as such a significant obstacle to membrane crossing—disappears. In other words, a single measure gives rise to a enhancement of the capability of a peptide or polypeptide to cross a biological barrier such as a cell membrane via two distinct mechanisms.

The common denominator of esters, thioesters and disulfides present in the peptide or polypeptide according to the invention is their reversibility under physiological conditions. Upon crossing a biological barrier such as a membrane said disulfides are in equilibrium with their reduced forms and said esters or thioesters are readily hydrolyzed or cleaved. The net effect is a peptide or polypeptide which is only transiently esterified or thio-esterified and/or only, transiently contains one or more disulfides. In the esterified/thio-esterified/disulfide form, the peptide or polypeptide exhibits enhanced delivery across biological barriers, whereas upon crossing said barrier a form of the peptide or polypeptide is recovered which is free or substantially free of the esters, thioesters or disulfides according to the invention and as such constitutes a peptide or polypeptide active agent delivery of which was intended. The term delivery refers to the transport of an agent to a site in an organism, tissue or cell. As a consequence, the derivatized form of the peptide or polypeptide, i.e. the peptide or polypeptide according to the invention, has a half-life which is sufficiently short to prevent an adverse reaction of the immune system.

A further consequence of the cleavage of the ester or thioester groups and the reduction of the disulfides after crossing the biological barrier is a shift of the equilibrium towards the translocated form. As a consequence, a peptide or polypeptide is effectively trapped within the biological barrier upon cleavage of the esters or thioesters or reduction of the disulfides.

Consistent therewith, the translocated peptide shows full biological activity as described in the examples enclosed herewith. For an illustration of this principle see FIG. 3.

Esterification and thio-esterification is particularly advantageous since esterases are known to be particularly active in tumors, in the brain and in the interior of cell. As such, the treatment of tumors and cancers with peptides or polypeptides according to the invention is particularly envisaged as is the delivery of peptide or polypeptide active agents across the blood brain barrier.

If all options (a) (i) to (v) and (b) are available, it is preferred to make use of options (i) and (ii), since thereby not only the desired guanidinium groups are introduced, but also the negative charges of the carboxylates which preclude crossing of biological barriers are removed.

As regards the length of the alkyl chain in the guanidinium alkanol, guanidinium alkanethiol or guanidinium alkanoic acid according to the invention, preference is given to longer alkyl chains such as alkyl chains with four or more carbon atoms.

As regards the spatial distribution of guanidinium groups in the peptide or polypeptide according to the invention, wherein the term "guanidinium group" includes guanidinium groups comprised in arginine residues, it is preferred that said guanidinium groups are homogeneously distributed across the sequence of said peptide or polypeptide to the extent possible. In other words, if possible, it is preferred to avoid clustering of guanidinium groups in one region of the peptide or polypeptide while the remainder of said peptide or polypeptide according to the invention is free or essentially free of guanidinium residues. Clustering, while not abolishing uptake of peptides or polypeptides according to the invention across a biological barrier, may reduce uptake to some extent as compared to a more homogenous distribution (see Rothbard et al., J. Med. Chem. 45, 3612-3618 (2002)). Homogenous distribution, i.e. avoiding of clustering can be achieved by either one of the following means. In case of peptides, in particular in case of peptides with 20 or less residues, the peptides according to the invention may be obtained by synthesis from the amino acid building blocks, wherein esterified amino acids are used at the desired positions. That is, for example, instead of Asp or Glu, one uses an Asp or Glu which is esterified at the side-chain carboxylate as defined above. In case of longer peptides and polypeptides this synthetic approach is less preferred. A homogenous distribution may then be obtained by controlling the molar ratio of the naturally occurring peptide or polypeptide or of the peptide or polypeptide the pharmacological properties of which are to be improved on the one side and of the above defined guanidinium group-containing compounds (guanidinium alkanoles, guanidinium alkanethiols, guanidinium alkanoic acids, PEGs substituted with a guanidinium group and having a free hydroxyl group, PEGs substituted with a guanidinium group and a sulfhydryl group and PEGs substituted with a guanidinium group and a carboxyl group) on the other side. Where necessary, denaturing conditions may be used which ensure that all functional groups to be esterified are equally accessible.

By avoiding the use of cell-penetrating peptides of the prior art as a means of enhancing the pharmacological properties such as delivery of peptide or polypeptide active agents, the production of such peptide or polypeptide active agents is rendered significantly more economical. Furthermore, possible long-term allergenic or immunogenic effects of said cell-penetrating peptides are avoided.

In those cases where the polypeptide or peptide according to the invention, as opposed to a peptide or polypeptide which is not esterified or thio-esterified according to any one of (i) to (iv), and which is not amidated and esterified or thio-esterified according to (v) and which does not contain disulfides according to (b), is not pharmaceutically active or is pharmaceutically active to a lower extent, the peptide or polypeptide according to the invention is a prodrug form. Cleavage of the ester and/or thioester and/or reduction of the disulfide upon delivery gives then rise to a pharmaceutically active peptide or polypeptide in a delayed and/or delivery-dependent manner, wherein delivery comprises crossing of a biological barrier.

In a preferred embodiment of the peptide or polypeptide according to the invention, the guanidinium alkanol or guanidinium alkanethiol has the following structure:

$$HX—(CR_1R_2)_n—N(R_3)—C(=NR_4)—NHR_5 \qquad \text{(Formula I)}$$

wherein:

X is O or S;

each occurrence of $R_1$ and $R_2$ is independently selected from H; halogen; $NH_2$; alkyl with 1 to 5 carbon atoms; aryl; and heteroaryl;

n is an integer number between 2 and 15;

$R_3$ is H or alkyl with 1 to 5 carbon atoms; and $R_4$ and $R_5$ are independently selected from H; alkyl with 1 to 5 carbon atoms; aryl;

heteroaryl, wherein the N bearing the $R_4$ or $R_5$ group may be a ring atom of the heteroaryl ring; and/or $R_4$ and $R_5$ may be selected together to give a heteroaryl ring.

In an alternative embodiment, larger values of n than those defined above are deliberately envisaged. Such larger values include values of n=20, 25 or 30.

In a more preferred embodiment, the guanidinium alkanol or guanidinium alkanethiol has the following structure:

$$HX—(CH_2)_n—NR—C(=NH)—NH_2 \qquad \text{(Formula II)}$$

wherein:

X is O or S;

n is an integer number between 2 and 10; and

R is H or alkyl with 1 to 5 carbon atoms.

In a further preferred embodiment, the guanidinium alkanoic acid has the following $$HOOC—(CR_1R_2)_n—N(R_3)—C(=NR_4)—NHR_5 \qquad \text{(Formula III)}$$

wherein:

each occurrence of $R_1$ and $R_2$ is independently selected from H; halogen; $NH_2$; alkyl with 1 to 5 carbon atoms; aryl; and heteroaryl;

n is an integer number between 2 and 15;

$R_3$ is H or alkyl with 1 to 5 carbon atoms; and $R_4$ and $R_5$ are independently selected from H; alkyl with 1 to 5 carbon atoms; aryl; heteroaryl, wherein the N bearing the $R_4$ or $R_5$ group may be a ring atom of the heteroaryl ring; and/or $R_4$ and $R_5$ may be selected together to give a heteroaryl ring.

In an alternative embodiment, larger values of n than those defined above are deliberately envisaged. Such larger values include values of n=20, 25 or 30.

Preferably, said guanidinium alkanoic acid is creatine or guandinino-acetic acid, the formulae of which are shown below:

$$HOOC—CH_2—N(CH_3)—C(=NH)—NH_2$$

(creatine)

$$HOOC—CH_2—NH—C(=NH)—NH_2$$

(guandinino-acetic acid)

In a more preferred embodiment, the guanidinium alkanoic acid has the following structure:

$$HOOC—CHR_1—(CH_2)_{n-1}—N(R_2)—C(=NH)—NH_2 \qquad \text{(Formula IV)}$$

wherein:

$R_1$ is H or $NH_2$;

n is an integer number between 2 and 10; and and $R_2$ is H or alkyl with 1 to 5 carbon atoms.

In one preferred embodiment, said guanidinium alkanoic acid is arginine, i.e. $R_1$ is $NH_2$; $R_2$ is H and n is 4.

Generally, preferred values of n are between 4 and 9, more preferred between 4 and 6.

In a preferred embodiment, said alkyl with 1 to 5 carbon atoms is methyl.

In a further preferred embodiment of the peptide or polypeptide of the invention, said PEG substituted with a guanidinium group and having a free hydroxyl group or said PEG substituted with a guanidinium group and a sulfhydryl group, respectively, has the following structure $$HX—CH_2CH_2(OCH_2CH_2)_k—N(R_3)—C(=NR_4)—NHR_5 \quad \text{(Formula V)}$$

wherein k is an integer number between 1 and 12 and X, $R_3$, $R_4$ and $R_5$ are as defined above.

In a further preferred embodiment of the peptide or polypeptide of the invention, said PEG substituted with a guanidinium group and a carboxyl group has the following structure $$HOOC—CH_2CH_2(OCH_2CH_2)_k—N(R_3)—C(=NR_4)—NHR_5 \quad \text{(Formula VI)}$$

wherein k is an integer number between 1 and 12 and X, $R_3$, $R_4$ and $R_5$ are as defined above. Alternatively, said PEG substituted with a guanidinium group and a carboxyl group has the following formula $$HOOC—CH_2(OCH_2CH_2)_k—N(R_3)—C(=NR_4)—NHR_5$$

Such a compound is available for example by reacting α-halo (α-bromo or α-iodo) acetic acid t-butyl ester with a free terminal hydroxy group of a PEG molecule carrying a protected guanidinium group (for example N,N' Bis-Z, or N-Tosyl protecting groups) at the other end. Final removal of t-butyl ester protecting groups under acidic conditions generates the desired compound ready to be esterified with hydroxyl groups as defined above, for example of a peptide or polypeptide.

Preferably k is 1 to 3.

In a preferred embodiment of the peptide or polypeptide of the invention, $—C(=NR_4)—NHR_5$ is pyrimidin-2-yl, quinazolin-2-yl, imdidazol-2-yl or benzimidazol-2-yl. In other words, and as stated in the preferred embodiments above, the guanidinium group of the guanidinium alkanols, guanidinium alkanethiols, guanidinium alkanoic acids, PEGs substituted with a guanidinium group and having a free hydroxyl group, PEGs substituted with a guanidinium group and a sulfhydryl group or PEGs substituted with a guanidinium group and a carboxyl group according to the invention may be comprised in a ring such as the heteroaryl rings mentioned above.

In a further preferred embodiment, said guanidinium alkanoic acid or said PEG substituted with a guanidinium group and a carboxyl group is not directly esterified or thioesterified with a hydroxyl or sulfhydryl group of a Ser, Thr, Tyr or Cys residue, respectively, but instead with a polymeric or oligomeric linker which in turn comprises a functional group available for esterification with a peptide or polypeptide. Preferably, and to explain further, said polymeric or oligomeric linker is a polyethylene glycol (PEG), or an alkyldiol, preferably an alkyl-1,ω-diol, or a poly-ols such as glycerol. Accordingly, preferred linkers have general formula $HO(CH_2CH_2O)_iH$ or $HO(CH_2)_jOH$ or $HO—CH_2—[(CH(OH)]_{(j-2)}—CH_2—OH$. Preferred values of i are the integer numbers from 1 to 10, more preferred 2, 3, 4 or 5. Preferred values of j are integer numbers from 1 to 20, preferably values between 2 and 10. If the guanidinium alkanoic acids or PEG substituted with a guanidinium group and a carboxyl group according to the invention are connected to such a linker, an ester bond is formed between the carboxylic group of the guanidinium alkanoic acid or the PEG substituted with a guanidinium group and a carboxyl group on the one side and a terminal hydroxyl group of the linker on the other side. As a consequence, a guanidinium group-containing moiety is obtained which has a terminal hydroxyl group available for esterification, the terminal hydroxyl group being that terminal hydroxyl group of the linker which is not engaged in the ester linkage between the linker and the guanidinium alkanoic acid or the PEG substituted with a guanidinium group and a carboxyl group according to the invention. The molecule obtained has a free hydroxyl group which can be esterified with carboxylates of a peptide or polypeptide. Accordingly, the molecule obtained can be esterified with the carboxylate of the C-terminus or with the side-chain carboxylates of one or more Asp or Glu residues, if present, of a peptide or polypeptide. In other words, said molecule may take the place of a guanidinium alkanol as recited in the main embodiment. Preferred guanidinium alkanoic acids which are esterified with a linker are shown below in formulae VI and VII, wherein preferred values of i and j are defined above and $R_1$, $R_2$, $R_3$, $R_4$ and $R_5$ are defined as described in conjunction with Formulae III and IV.

$$HO(CH_2CH_2O)_iC(=O)—(CR_1R_2)_n—N(R_3)—C(=NR_4)—NHR_5 \quad \text{(Formula VIII)}$$

$$HO(CH_2)_jOC(=O)—(CR_1R_2)_n—N(R_3)—C(=NR_4)—NHR_5 \quad \text{(Formula IX)}$$

The same applies mutatis mutandis to PEGs substituted with a guanidinium group and a carboxyl group.

In a further preferred embodiment of the peptide or polypeptide of the invention, (a) the carboxylate of the C-terminus, if not esterified or thioesterified as defined above, is esterified with a fatty alcohol; and/or (b) the amino group of the N-terminus, if not amidated with a alpha- or beta-hydroxy acid, is amidated with a fatty acid. The terms “amidated” or “amidation” refer to the formation of an amide bond —CO—NH— between a carboxylate and an amino group.

The presence of a fatty alcohol and/or of a fatty acid in the peptide or polypeptide of the invention enhances the hydrophobicity of said peptide or polypeptide and thereby increases the affinity to the lipophilic environment of the lipid bilayer of the membrane which is to be crossed in the course of delivery. As such, the peptide or polypeptide according to this preferred embodiment comprises two distinct types of moieties facilitating membrane attachment and internalisation, namely the hydrophobic groups provided by said fatty alcohol and/or said fatty acid and one or more guanidinium groups.

A fatty acid according to the invention is a carboxylic acid with a long aliphatic tail. The tail is either saturated or unsaturated and is preferably unbranched. The fatty acid according to the invention has at least four carbon atoms. Preferably, the number of carbon atoms of said fatty acid does not exceed 30.

A fatty alcohol according to the invention is a primary of secondary alcohol having at least four carbon atoms. Fatty alcohols according to the invention may be saturated or unsaturated. Preferably, the number of carbon atoms of said fatty alcohol does not exceed 30.

In a preferred embodiment, said fatty alcohol and/or said fatty acid contains between 5 and 15 carbon atoms, preferably 9 carbon atoms.

Accordingly, preferred fatty alcohols include 1-pentanol, 1-hexanol, 1-heptanol, 1-octanol, 1-nonanol, 1-decanol, 1-undecanol, 1-dodecanol, 1-tridecanol, 1-tetradecanol and 1-pentadecanol. Analogously, preferred fatty acids according to the invention include pentanoic acid, hexanoic acid, heptanoic acid, octanoic acid, nonanoic acid, decanoic acid, undecanoic acid, dodecanoic acid, tridecanoic acid, tetradecanoic acid and pentadecanoic acid. More preferred are 1-nonanol and nonanoic acid, respectively.

In a further preferred embodiment of the peptide or polypeptide of the invention, the number of guanidinium groups including those of any Arg residue(s), if present, is between 4 and 20, more preferred between 7 and 15, and most preferred 9, wherein at least one guanidinium group is comprised in a guanidinium alkanol, guanidinium alkanethiol, guanidinium alkanoic acid, PEG substituted with a guanidinium group and having a free hydroxyl group, PEG substituted with a guanidinium group and a sulfhydryl group or PEG substituted with a guanidinium group and a carboxyl group as defined above. It is also preferred that the peptide or polypeptide according the invention bears no net negative charges. Accordingly, if the total number of carboxylates of all Asp and Glu residues and including the C-terminal carboxylate exceeds 20, it is preferred that the peptide or polypeptide of the invention is esterified at all said carboxylates.

In a preferred embodiment of the peptide or polypeptide of the invention, said peptide or polypeptide is part of a peptide-PNA chimera. The term "PNA" refers to "peptide nucleic acid" and is further discussed below.

The present invention also relates to a nucleic acid (a) which is esterified at one or more of the following positions with a guanidinium alkanoic acid or a PEG substituted with a guanidinium group and a carboxyl group: (i) 5'-terminal 5' hydroxyl group; (ii) 3'-terminal 3' hydroxyl group; (iii) 5'- or 3'-terminal 2' hydroxyl group; and (iv) internal 2' hydroxyl group; (b) which is esterified at one, more or all phosphates with a guanidinium alkanol or a PEG substituted with a guanidinium group and having a free hydroxyl group; and/or (c) which has a 2' hydroxyl group converted into an acetal with a guanidinium alkanol or with a PEG substituted with a guanidinium group.

In a preferred embodiment, only option (b) is used.

Preferably, said acetal is a formaldehyde acetal. Alternatively, the aldehyde component of said acetal may be an aldehyde other than formaldehyde and has the general formula $R_a$—CHO, wherein $R_a$ is defined herein below. Means and methods of converting said 2' hydroxyl group into an acetal are described in the art and referred to further below.

To the extent reference is made to 2' hydroxyl groups, it is understood that the nucleic acid according to the invention is or comprises RNA. Methods for derivatizing the 2' hydroxyl position of oligoribonucleotides are known in the art and described in, for example, Rastogi and Usher (Nucleic Acids Research 23, 4872-4877 (1995)). Further types of nucleic acid, i.e., in addition to RNA, which are explicitly envisaged are discussed further below.

Figure 6:
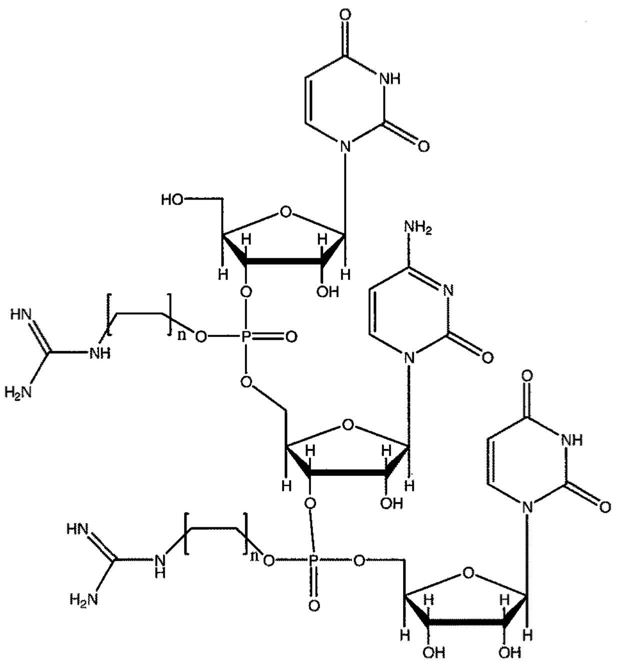

An example of a nucleic acid is shown in FIG. 6. The phosphates shown in FIG. 6 are engaged in three ester bonds, two of which are with the secondary hydroxyl groups of the ribose, and the third is with a guanidinium alkanol as defined above. Under in vivo conditions, the ester with the guanidinium alkanol will be hydrolyzed or cleaved by esterases since (i) the hydroxyl group of the guanidinium alkanol is a primary hydroxy group and (ii) the corresponding phosphate ester is located toward the external accessible surface of the nucleic acid of the invention. This does not apply to the ester bonds which are part of the sugar-phosphate backbone which are accordingly more stable.

Figure 7:
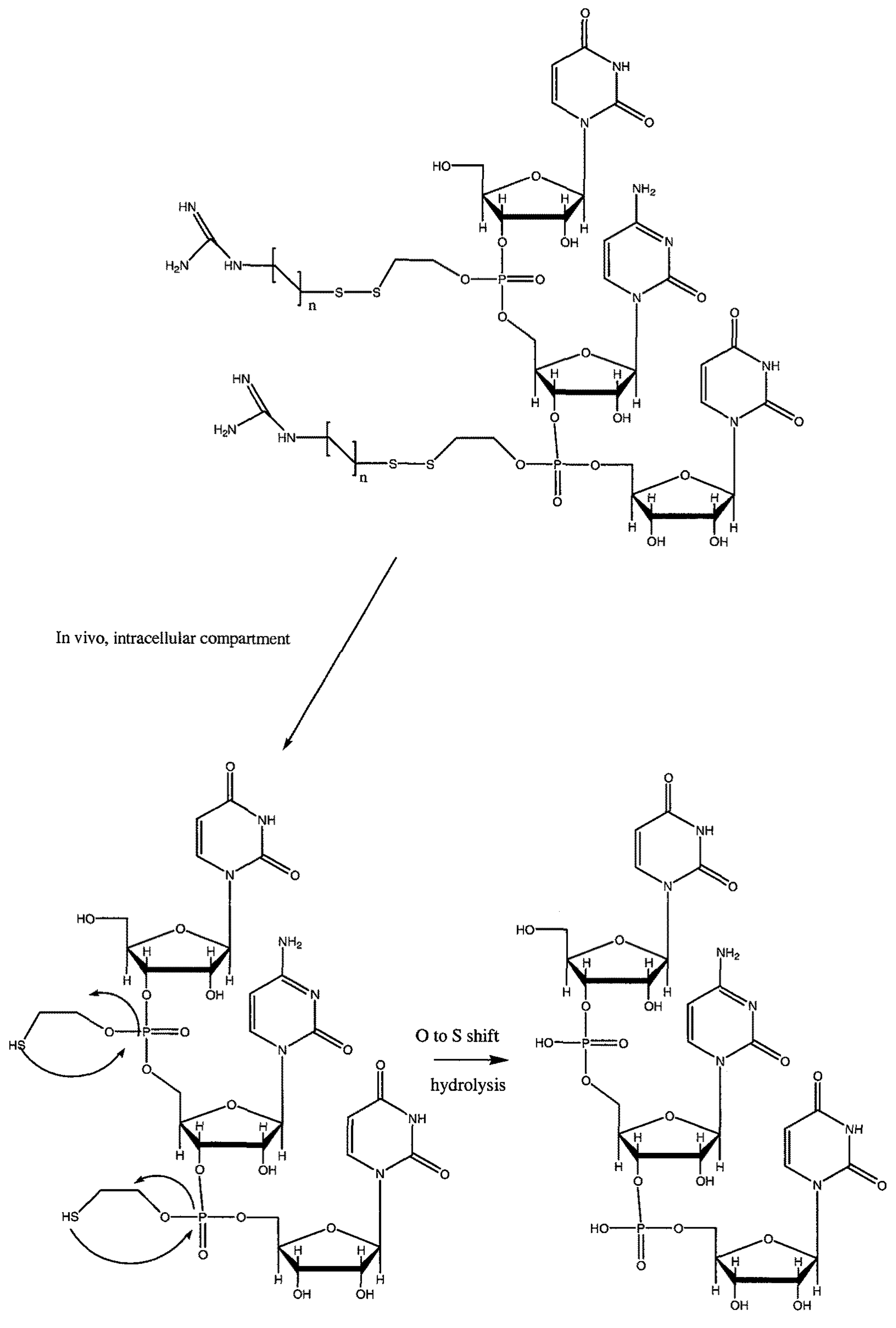

In a further preferred embodiment, the ester with a guanidinium alkanol or the ester with a fatty alcohol at one, more or all phosphates of the nucleic acid of the invention can be cleaved in vivo via a two-steps mechanism. As described for example by Parang et al. (Current Medicinal Chemistry, 2000, 7, 995-1039), phosphates can be cleaved via intramolecular elimination triggered by a first cleavage by which a functionality amenable to intramolecular rearrangement is set free. An example is provided in FIG. 7. In FIG. 7 cleavage of the sulfide causes formation a 2-mercapto ester, which in turn undergoes intramolecular cleavage via formation of thiirane. In analogy, also a "safety catch" strategy also envisaged, wherein a construct with an electron-withdrawing group like a ketone in β-position to the alcohol can be temporarily protected as acetal (not electron-withdrawing). Post-synthesis removal or in vivo cleavage of the acetal releases the electron-withdrawing ketone group and thus promotes phosphate cleavage via β-elimination.

In a further preferred embodiment, one or more terminal phosphates, if not esterified with a guanidinium alkanol, are esterified with a fatty alcohol.

Since phosphoric acid is a three-basic acid, terminal phosphates may be esterified with one or two equivalents alcohol. Accordingly, a terminal phosphate may be esterified with one equivalent guanidinium alkanol and one equivalent fatty alcohol.

Also, esterification of a terminal phosphate is two equivalents fatty alcohol is envisaged. Also, only one equivalent alcohol, either guanidinium alkanol or fatty alcohol may be linked to terminal phosphate.

The term "nucleic acid" as used herein embraces both single-stranded and double-stranded nucleic acids.

Preferred double-stranded nucleic acids according to the invention are esterified with one equivalent fatty alcohol at one terminal phosphate (5'-terminal phosphate of the first strand) and with one equivalent guanidinium alkanol at the other terminal phosphate (5'-terminal phosphate of the second strand). Optionally, in preferred double-stranded nucleic acids according to the invention one or more of positions (a)(i) to (iv) and/or (b) as defined above may be esterified as defined above. It is understood that in this case the phosphates according to (b) are internal phosphates.

Preferred single-stranded nucleic acids according to the invention are esterified with one equivalent fatty alcohol at the 5'-terminal phosphate and with at least one equivalent guanidinium alkanol at one or more of positions (b) as defined above. It is understood that in this case the phosphates according to (b) are internal phosphates. Alternatively or in addition to being esterified with a guanidinium alkanol at one or more internal phosphates, said preferred single-stranded nucleic acids according to the invention are esterified with one or more guanidinium alkanoic acids at one or more of positions (a)(i) to (iv) as defined above.

Analogous to the esterification of carboxylates in peptides or polypeptides according to the invention, the esterification of phosphates in nucleic acids according to the invention serves a two-fold purpose: (i) introduction of guanidinium groups; and (ii) removal of negative charges. Both aims are achieved with a single measure which is esterification with a guanidinium alkanol.

In a further preferred embodiment, said guanidinium alkanoic acid or said PEG substituted with a guanidinium group and a carboxyl group is not directly esterified with a hydroxyl group of a nucleic acid as defined in any one of (a)(i) to (iv), but instead with a polymeric or oligomeric linker which in turn comprises a functional group available for esterification with a nucleic acid. Preferably, and to explain further, said polymeric or oligomeric linker is a polyethylene glycol (PEG), or an alkyl-diol, preferably an alkyl-1,ω-diol, or a poly-ols such as glycerol. Accordingly, preferred linkers have general formula $HO(CH_2CH_2O)_iH$ or $HO(CH_2)_jOH$ or $HO—CH_2—[(CH(OH)]_{(j-2)}—CH_2—OH$. Preferred values of i are the integer numbers from 1 to 10, more preferred 2, 3, 4 or 5. Preferred values of j are integer numbers from 1 to 20, preferably values between 2 and 10. If the guanidinium alkanoic acids or PEG substituted with a guanidinium group and a carboxyl group according to the invention are connected to such a linker, an ester bond is formed between the carboxylic group of the guanidinium alkanoic acid or the PEG substituted with a guanidinium group and a carboxyl group on the one side and a terminal hydroxyl group of the linker on the other side. As a consequence, a guanidinium group-containing moiety is obtained which has a terminal hydroxyl group available for esterification, the terminal hydroxyl group being that terminal hydroxyl group of the linker which is not engaged in the ester linkage between the linker and the guanidinium alkanoic acid or the PEG substituted with a guanidinium group and a carboxyl group according to the invention. In other words, the molecule obtained has a free hydroxyl group which can be esterified with a phosphate of a nucleic acid. Accordingly, the molecule obtained can be esterified with a phosphate of the nucleic acid as defined in (b) above. That is, said molecule may take the place of a guanidinium alkanol as recited in item (b) of the embodiment relating to nucleic acid according to the invention. Preferred guanidinium alkanoic acids which are esterified with a linker are shown herein above; see formulae VI and VII. The same applies mutatis mutandis to PEGs substituted with a guanidinium group and a carboxyl group.

In a further preferred embodiment, said nucleic acid is a DNA, RNA or siRNA. Nucleic acid molecules, in accordance with the present invention, include DNA, such as cDNA or genomic DNA, and RNA. It is understood that the term "RNA" as used herein comprises all forms of RNA including mRNA, ncRNA (non-coding RNA), tRNA and rRNA. The term "non-coding RNA" includes siRNA (small interfering RNA), miRNA (micro RNA), rasiRNA (repeat associated RNA), snoRNA (small nucleolar RNA), and snRNA (small nuclear RNA). Preferably, embodiments reciting "RNA" are directed to mRNA. At the same time, other forms of RNA, including the above mentioned specific forms, are deliberately envisaged in the respective embodiments. Furthermore included is genomic RNA, such as in case of RNA of RNA viruses.

Further included are nucleic acid mimicking molecules known in the art such as synthetic or semisynthetic derivatives of DNA or RNA and mixed polymers, both sense and antisense strands. They may contain additional non-natural or derivatized nucleotide bases, as will be readily appreciated by those skilled in the art. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA) (see, for example, Braasch and Corey, Chemistry & Biology 8, 1-7 (2001)). LNA is an RNA derivative in which the ribose ring is constrained by a methylene linkage between the 2'-oxygen and the 4'-carbon.

For the purposes of the present invention, a peptide nucleic acid (PNA) is a polyamide type of DNA analog. The monomeric units for the corresponding derivatives of adenine, guanine, thymine and cytosine are available commercially (for example from Perceptive Biosystems). PNA is a synthetic DNA-mimic with an amide backbone in place of the sugar-phosphate backbone of DNA or RNA. As a consequence, certain components of DNA, such as phosphorus, phosphorus oxides, or deoxyribose derivatives, are not present in PNAs. As disclosed by Nielsen et al., Science 254:1497 (1991); and Egholm et al., Nature 365:666 (1993), PNAs bind specifically and tightly to complementary DNA strands and are not degraded by nucleases. Furthermore, they are stable under acidic conditions and resistant to proteases (Demidov et al. (1994), Biochem. Pharmacol., 48, 1310-1313). Their electrostatically neutral backbone increases the binding strength to complementary DNA as compared to the stability of the corresponding DNA-DNA duplex (Wittung et al. (1994), Nature 368, 561-563; Ray and Norden (2000), Faseb J., 14, 1041-1060). In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point ($T_m$) by 8°-20° C., vs. 4°-16° C. for the DNA/DNA 15-mer duplex. Thereby discrimination between perfect matches and mismatches is improved. For its uncharged nature, PNA also permits the hybridisation of DNA samples at low salt or no-salt conditions, since no inter-strand repulsion as between two negatively charged DNA strands needs to be counteracted. As a consequence, the target DNA has fewer secondary structures under hybridisation conditions and is more accessible to probe molecules.

It is furthermore envisaged that said nucleic acid according to the invention is a PNA. A PNA may be derivatized at the α-carbon of the polyamide backbone by introduction of a moiety bearing a guanidinium group, thereby obtaining a nucleic acid according to the invention which is a PNA.

PNA chimera according to the present invention are molecules comprising one or more PNA portions. The remainder of the chimeric molecule may comprise one or more DNA portions (PNA-DNA chimera) or one or more (poly)peptide portions ((poly)peptide-PNA chimera). (Poly)peptide-DNA chimera according to the invention are molecules comprising one or more (poly)peptide portions and one or more DNA portions. Molecules comprising PNA, peptide and DNA portions are envisaged as well. The length of a portion of a chimeric molecule may range from 1 to N-1 bases, equivalents thereof or amino acids, wherein "N" is the total number of bases, equivalents thereof and amino acids of the entire molecule.

The term "derivatives" in conjunction with the above described PNAs, (poly)peptides, PNA chimera and peptide-DNA chimera relates to molecules wherein these molecules comprise one or more further groups or substituents different from PNA, (poly)peptides and DNA. All groups or substituents known in the art and used for the synthesis of these molecules, such as protection groups, and/or for applications involving these molecules, such as labels and (cleavable) linkers are envisaged.

The present invention furthermore relates to a liposome or micelle bearing one or more guanidinium groups, wherein the one or more guanidinium groups are linked to the liposome or micelle by a functional group which is cleavable under physiological conditions.

A liposome according to the invention is a vesicle, preferably spherical vesicle, with a membrane bilayer comprising phospholipids and optionally cholesterol. Liposomes may comprise naturally-derived phospholipids with mixed lipid chains (like egg phosphatidylethanolamine), or of pure surfactant components like DOPE (dioleolylphosphatidylethanolamine). Liposomes, usually, but not by definition, contain a core of aqueous solution. Liposomes are used for drug delivery due to their unique properties. For the purpose of the present invention, liposomes are envisaged the delivery of which to biological systems is desired, such as liposomes containing one or more pharmaceutically active agents in their interior. A liposome may encapsulate a region of aqueous solution inside the hydrophobic membrane; dissolved hydrophilic solutes can not readily pass through the lipids. Hydrophobic chemicals can be dissolved into the membrane, and in this way liposome can carry both hydrophobic molecules and hydrophilic molecules. To deliver the molecules to sites of action, the lipid bilayer of the liposome can fuse with other bilayers such as the cell membrane, thus delivering the liposome contents. By making liposomes in a solution of agents such as DNA or drugs (which would normally be unable to diffuse through the membrane), said agents can be (indiscriminately) delivered past the lipid bilayer. The use of liposomes for transformation or transfection of DNA into a host cell is known as lipofection. Further advances in liposome research have been able to allow liposomes to avoid detection by the body's immune system, specifically, the cells of reticuloendothelial system (RES). These liposomes are known as "stealth liposomes", and are constructed with PEG (Polyethylene Glycol) studding the outside of the membrane. The PEG coating, which is inert in the body, allows for longer circulatory life for the drug delivery mechanism.

A micelle according to the invention is an aggregate of surfactant molecules, usually dispersed in a liquid. A typical micelle in aqueous solution forms an aggregate with the hydrophilic "head" regions in contact with surrounding solvent, sequestering the hydrophobic tail regions in the micelle centre. Alternatively, the micelle may have a bilayer structure. The center of the micelle may comprise further substances, for example substances, such as pharmaceutically active agents the delivery of which to biological systems is desired. Generally, micelles are approximately spherical in shape. The shape and size of a micelle is a function of the molecular geometry of its surfactant molecules and solution conditions such as surfactant concentration, temperature, pH, and ionic strength.

Micelles are generally cholesterol-free. It is preferred that both liposomes and micelles according to the invention are cholesterol-free, or, in case cholesterol is present, said cholesterol is unmodified, naturally occurring cholesterol.

For the purpose of this invention, it is important that all said guanidinium groups or a significant fraction thereof are located at the outer surface of said liposome or micelle.

In a preferred embodiment, said functional group is an ester group. Further functional groups according to the invention which are cleavable under physiological conditions are acetal, disulfide, thioester, and phosphate ester.

In a further preferred embodiment, said liposome or micelle is esterified (a) at one or more hydroxyl groups with a guanidinium alkanoic acid or a PEG substituted with a guanidinium group and a carboxyl group; and/or (b) at one or more acidic groups such as phosphate and carboxylate with a guanidinium alcohol, a guanidinium alkanethiol, a PEG substituted with a guanidinium group and having a free hydroxyl group, or a PEG substituted with a guanidinium group and a sulfhydryl group.

Preferably, said hydroxyl group is a primary hydroxyl group, i.e., a hydroxyl group bound to a fragment —$CH_2R$. Primary hydroxyl groups yield upon esterification an ester which is cleaved more rapidly and/or to a greater extent as compared to secondary or tertiary hydroxyl groups. More rapid cleavage and/or cleavage to a greater extent are preferred since they entail a more rapid formation and/or formation to a larger extent of a form of the liposome or micelle which is free of or substantially free of said guanidinium groups, attachment of which serves the purpose of transiently enhancing the capability of crossing biological barriers such as biological membranes.

In a further preferred embodiment of the liposome or micelle according to the invention, a primary amino group of said liposome or micelle is converted into a guanidinium group. A primary amino group can be converted into a guanidinium structure by using commercially available or known "guanidylation reagents". Suitable means and methods for the guanidinylation of primary amines are described in, for example, Feichtinger et al. (J. Org. Chem. 63, 8432-8439 (1998)) or Brand and Brand (Organic Syntheses 3, 440 (1955)). According to Feichtinger et al. both nitrogens of the guanidylation reagents are protected and the reaction occurs with high yields in organic solvents. Then, upon reaction completion, the protecting group must be removed, principally via acid cleavage. According to Brand and Brand, the guanidylation agent is kept as salt (the nitrogens are not covalently protected) in an unreactive form. Then, upon addition of the primary amine in water/aqueous mixture at basic pH, the desired product is obtained. The latter procedure avoids final removal of protecting groups.

In a further preferred embodiment, the hydroxyl group is a hydroxyl group of a lipid selected from phosphatidyl inositol, phosphatidyl glycerol, mono-acyl glycerol, and di-acyl glycerol, wherein said lipid is comprised in the liposome or micelle; or a terminal hydroxyl group of a PEG moiety comprised in the liposome or micelle. The use PEG moieties as polar headgroups of constituents of liposomes and micelles is known in the art.

Preferably, said primary amino group is a primary amino group of phosphatidyl ethanolamine or of a PEG moiety wherein the terminal hydroxyl moiety of said PEG moiety is replaced with a primary amino group.

Preferably, the guanidinium alkanol, guanidinium alkanethiol, guanidinium alkanoic acid, PEG substituted with a guanidinium group and having a free hydroxyl group, PEG substituted with a guanidinium group and a sulfhydryl group, and PEG substituted with a guanidinium group and a carboxyl group comprised in the nucleic acid, liposome or micelle of the invention is as defined herein above in conjunction with peptides and polypeptides according to the invention. Further explanations as well as further preferred embodiments relating to these compounds apply mutatis mutandis also to nucleic acids, liposomes and micelles according to the invention.

The present invention also relates to a pharmaceutical composition comprising a peptide or polypeptide according to the invention and/or nucleic acid according to the invention and/or a liposome or micelle according to the invention.

The pharmaceutical composition may further comprise pharmaceutically acceptable carriers, excipients and/or diluents. Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. The compositions may also be administered directly to the target site, e.g., by biolistic delivery (also referred to as "gene gun") to an external or internal target site. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 ng and 10 mg/kg body weight per dose; however, doses below or above this exemplary range are envisioned, especially considering the aforementioned factors. If the regimen is a continuous infusion, it should also be in the range of 1 μg to 10 mg units per kilogram of body weight per minute.

The present invention furthermore provides a method of enhancing the capability of a polymer, liposome or micelle to cross a biological barrier, the polymer having, liposome or micelle one or more carboxyl, hydroxyl, sulfhydryl, and/or phosphate groups, comprising the step of modifiying at least one of said groups to give Formula VII

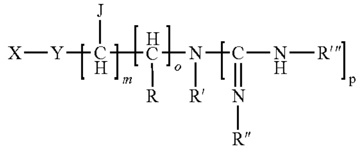

wherein independently for each occurrence of Formula VII (a) X is —(C═O); Y is O or S;

(b) X is —O or —S; Y is (C═O) or ($CHR_a$)—O;

(c) X—Y is —S—S; or (d) X is —O—P(═O)$OR_p$; Y is O or S; and each occurrence of J is independently selected from H; halogen; $NH_2$; alkyl with 1 to 15 carbon atoms; and $[CHR]_o$—NR'—CH(NHR")—NH—R'";

each occurrence of R, R', R", R'", $R_a$ and $R_p$ is independently selected from H; alkyl with 1 to 15 carbon atoms; and substituted or unsubstituted aryl; wherein R and R'; R' and R"; and/or R" and R'" may be selected together form a cyclic structure; alkyl may be substituted;

m is an integer number between 0 and 10; wherein if J is $[CHR]_o$—NR'—CH(NHR")—NH—R'", then m is 1;

o is an integer number between 1 and 15; and p is 0 or 1; wherein if p is 0, then the free valence of N bearing R' is filled with H.

Formula VII includes said carboxyl, hydroxyl, sulfhydryl or phosphate group modification of which by the method of the invention is envisaged. Accordingly, the fragment X-Y is an ester or thioester group in case of (a), an ester, thioester or acetal group in case of (b), a disulfide in case of (c) and a phosphate or thiophosphate in case of (d). X contains a free valence, as indicated in (a) to (d), which is the bond connecting the carboxyl, hydroxyl, sulfhydryl or phosphate group to be modified to said polymer liposome or micelle.

Since J may also be $[CHR]_o$—NR'—CH(NHR")—NH—R'", the method according to the invention allows to introduce a bis-guanidinium substituent at any one of said carboxyl, hydroxyl, sulfhydryl or phosphate groups.

Preferably, the sum of m and o is 4, 5 or 6. Also preferred is that alkyl is methyl.

In a preferred embodiment of the method of the invention, said polymer is a peptide, polypeptide or nucleic acid.

Accordingly, the above-described peptides, polypeptides or nucleic acids according to the invention are obtainable via the method of the invention.

The present invention also provides a method of enhancing the capability of a peptide or polypeptide to cross a biological barrier, comprising the step of (a) formation of one or more esters or thioesters (i) at the carboxylate of the C-terminus with a guanidinium alkanol, a guanidinium alkanethiol, a PEG substituted with a guanidinium group and having a free hydroxyl group, or a PEG substituted with a guanidinium group and a sulfhydryl group; (ii) at a side-chain carboxylate of one or more Asp or Glu residues, if present, with a guanidinium alkanol, a guanidinium alkanethiol, a PEG substituted with a guanidinium group and having a free hydroxyl group, or a PEG substituted with a guanidinium group and a sulfhydryl group; (iii) at a hydroxyl group of one or more Ser, Thr or Tyr residues, if present, with a guanidinium alkanoic acid; (iv) at a sulfhydryl group of one or more Cys residues, if present, with a guanidinium alkanoic acid or a PEG substituted with a guanidinium group and a carboxyl group; and/or (v) at the N-terminus with a guanidinium alkanoic acid or a PEG substituted with a guanidinium group and a carboxyl group, wherein said N-terminus is previously amidated with an alpha- or beta-hydroxy acid, and wherein the ester is formed between the hydroxy group of said alpha- or beta-hydroxy acid and the carboxylic group of said guanidinium alkanoic acid or said PEG substituted with a guanidinium group and a carboxyl group; and/or (b) formation of one or more disulfides, the disulfide being formed between the sulfhydryl group of a Cys reside, if present, and a guanidinium alkanethiol or a PEG substituted with a guanidinium group and a sulfhydryl group.

Definitions, advantages and preferred embodiments of the main embodiment of the invention described herein above apply mutatis mutandis also to the above-described method of enhancing the capability of a peptide or polypeptide to cross a biological barrier according to the invention.

In a preferred embodiment of the methods according to the invention, the biological barrier is selected from a cell membrane, a mucosa, and the blood-brain-barrier.

In a further preferred embodiment, the method of enhancing the capability of a peptide or polypeptide to cross the biological barrier according to the invention, said method further comprises the step of (a) formation of an ester or thioester at the carboxylate of the C-terminus with a fatty alcohol, if said C-terminus is not esterified as defined above; and/or (b) amidation of the amino group of the N-terminus with a fatty acid.

In a more preferred embodiment, said fatty alcohol and/or said fatty acid contains between 5 and 15 carbon atoms, preferably 9 carbon atoms.

Definitions, advantages and preferred embodiments relating to said fatty acid or said fatty alcohol, respectively, and described herein above in conjunction with the peptide or polypeptide of the invention apply mutatis mutandis to the present method.

In a further preferred embodiment, the number of guanidinium groups upon formation of esters, thioesters, acetates, disulfides and/or phosphate esters, wherein said number of guanidinium groups includes those of any Arg residue(s), if present, is between 5 and 20, more preferred between 7 and 15, and most preferred 9.

Furthermore, the present invention provides a method of enhancing the capability of a nucleic acid to cross a biological barrier, comprising the step of (a) forming an ester with a guanidinium alkanoic acid or a PEG substituted with a guanidinium group and a carboxyl group at one or more of the following positions: (i) 5'-terminal 5' hydroxyl group; (ii) 3'-terminal 3' hydroxyl group; (iii) 5'- or 3'-terminal 2' hydroxyl group; and (iv) internal 2' hydroxyl group; (b) forming an ester with a guanidinium alkanol or a PEG substituted with a guanidinium group and having a free hydroxyl group at one or more phosphates; and/or forming an acetal between a 2' hydroxyl group and a guanidinium alkanol or a PEG substituted with a guanidinium group.

Preferably, said acetal is a formaldehyde acetal. Alternatively, the aldehyde component of said acetal may be an aldehyde other than formaldehyde and has the general formula $R_a$—CHO, wherein $R_a$ is defined herein below.

A nucleic acid which is esterified at the phosphate group with a guanidinium alkanol or a PEG substituted with a guanidinium group can be prepared by a modified standard protocol (Vinayak et al., Nucleic Acids Research, 20, 1265-1269 (1992); Ogilvie et al., P.N.A.S. 85, 5764-5768 (1988)). Instead of the standard cyanoethyl protecting group, which is removed under basic conditions employed to cleave the biopolymer from the solid support, a guanidinium alkanol or a PEG substituted with a guanidinium group which is protected with a base-labile group (Fmoc) or reduction-labile moieties (Nitro, Benzyl, trichloroethyl) can be employed. In case of a base-labile guanidinium protecting group, the final basic treatment to detach the synthesized oligonucleotide will concomitantly remove the guanidinium protecting group. In case of a guanidinium protecting group which is cleavable under reducing conditions, an additional step under reducing conditions is required after cleavage of the oligonucleotide from the solid support to finally remove the guanidinium protecting group.

A nucleic acid, which is derivatized at the 2' position with a guanidinium alkanol or a PEG substituted with a guanidinium group via an acetal group can be prepared by a modified standard protocol (for example Rastogi et. al., Nucleic Acids Research 23, 4872-4873 (1995)). A guanidinium alkanol or a PEG substituted at one end with a guanidinium group can be used to form an acetal with the hydroxyl group at the 2' position. The acetal will be stable during the cleavage of the oligonucleotide from the solid support.

In a further preferred embodiment, said method further comprises esterifying one or more terminal phosphates with a fatty alcohol.

Definitions, advantages and preferred embodiments as described in conjunction with the nucleic acid according to the invention apply mutatis mutandis to the method of enhancing the capability of a nucleic acid to cross a biological barrier according to the invention.

The present invention furthermore provides a method of enhancing the capability of a liposome or micelle to cross a biological barrier, comprising the step of (a) forming an ester with a guanidinium alkanoic acid or a PEG substituted with a guanidinium group and a carboxyl group at one or more hydroxyl groups of said liposome or micelle; and/or (b) forming an ester with a guanidinium alcohol, a guanidinium alkanethiol, a PEG substituted with a guanidinium group and having a free hydroxyl group, or a PEG substituted with a guanidinium group and a sulfhydryl group at one or more acidic groups such as phosphate or carboxylate; and/or (c) converting a primary amino group of said liposome or micelle into a guanidinium group.

Preparation of a liposome or micelle according to the invention may be effected by using a guanidinium alkanoic acid or a PEG substituted with a guanidinium group and a carboxyl group to form an ester at one or more hydroxyl groups of said liposome or micelle. Hydroxyl groups of said liposomes or micelles may be provided by constituent amphiphilic lipids such as phosphatidylglycerol. For example, a phosphatidylglycerol or a phosphatidyldi-ol (a phospholipid with the phosphate esterified with an alkyl or PEG chain that has two free ends each bearing a hydroxyl group) is esterified at a free terminal hydroxyl or sulfhydryl group with a guanidinium carboxylic acid. For example, commercially available N,N'-bis-tert-butoxycarbonyl guanidinium acetic acid can be coupled to phosphatidylglycerol in a DMF/DCM mixture via DCC-HOBT-DMAP coupling. After purification, TFA treatment removes the bis-Boc groups and generates the desired compound.

Preparation of a liposome or micelle according to the invention can also be effected by using a guanidinium alcohol, a guanidinium alkanethiol, a PEG substituted with a guanidinium group and having a free hydroxyl group or a PEG substituted with a guanidinium group and a sulfhydryl group which is esterified, for example, with a phosphatidylserine, phosphatidyl-serine being a constituent of said liposome or micelle. In this case, the free carboxylate of the amino acid moiety (serine) is esterified with said guanidinium alcohol, guanidinium alkanethiol, PEG substituted with a guanidinium group and having a free hydroxyl group, or with said PEG substituted with a guanidinium group and a sulfhydryl group.

Converting a primary amino group of said liposome or micelle into a guanidinium group can easily be effected by treating for example a cationic surfactant that has a primary amino group like phosphatidyl ethanolamine (said cationic surfactant being a constituent of said liposome or micelle), with an excess of a reagent capable of converting a primary amine into a guanidinium group such as 1,3-di-Boc-2-methylisothiourea. For example, phosphatidyl ethanolamine can be reacted in DCM (dichloromethane) with a 2 to 3 equivalents of 1,3-di-Boc-2-methylisothiourea in presence of a non-nucleophilic base (such as TEA or DIEA) at room temperature for 24 to 48 hrs. Reaction can be monitored by UV-ninhydrine monitoring. Upon evaporation of the solvent and isolation of the reacted material, final treatment with TFA necessary to cleave the Boc group generates the desired product with free guanidinium groups.

Methods of converting a primary amino group into a guanidinium group are described herein above.

Definitions, advantages and preferred embodiments as they are described herein in conjunction with liposomes and micelles according to the invention apply mutatis mutandis to the method of enhancing the capability of a liposome or micelle to cross a biological barrier according to the invention. In particular, said guanidinium alkanol, said guanidinium alkanethiol, said guanidinium alkanoic acid, said PEG substituted with a guanidinium group and having a free hydroxyl group, said PEG substituted with a guanidinium group and a sulfhydryl group, and said PEG substituted with a guanidinium group and a carboxyl group are preferably as defined herein above.

The Figures show:

FIG. 1: Exemplary Glu residues modified according to the invention (left, middle) compared to a native Arg residue (right). The Glu residue is embedded in a peptidic context as indicated by the free valences on the main chain nitrogen and carbonyl carbon.

FIG. 2: Schematic drawing of a peptide comprising native Lys and Arg residues as well as Asp or Glu residues (left), wherein Asp and Glu residues are modified according to the invention (right).

Figure 3:
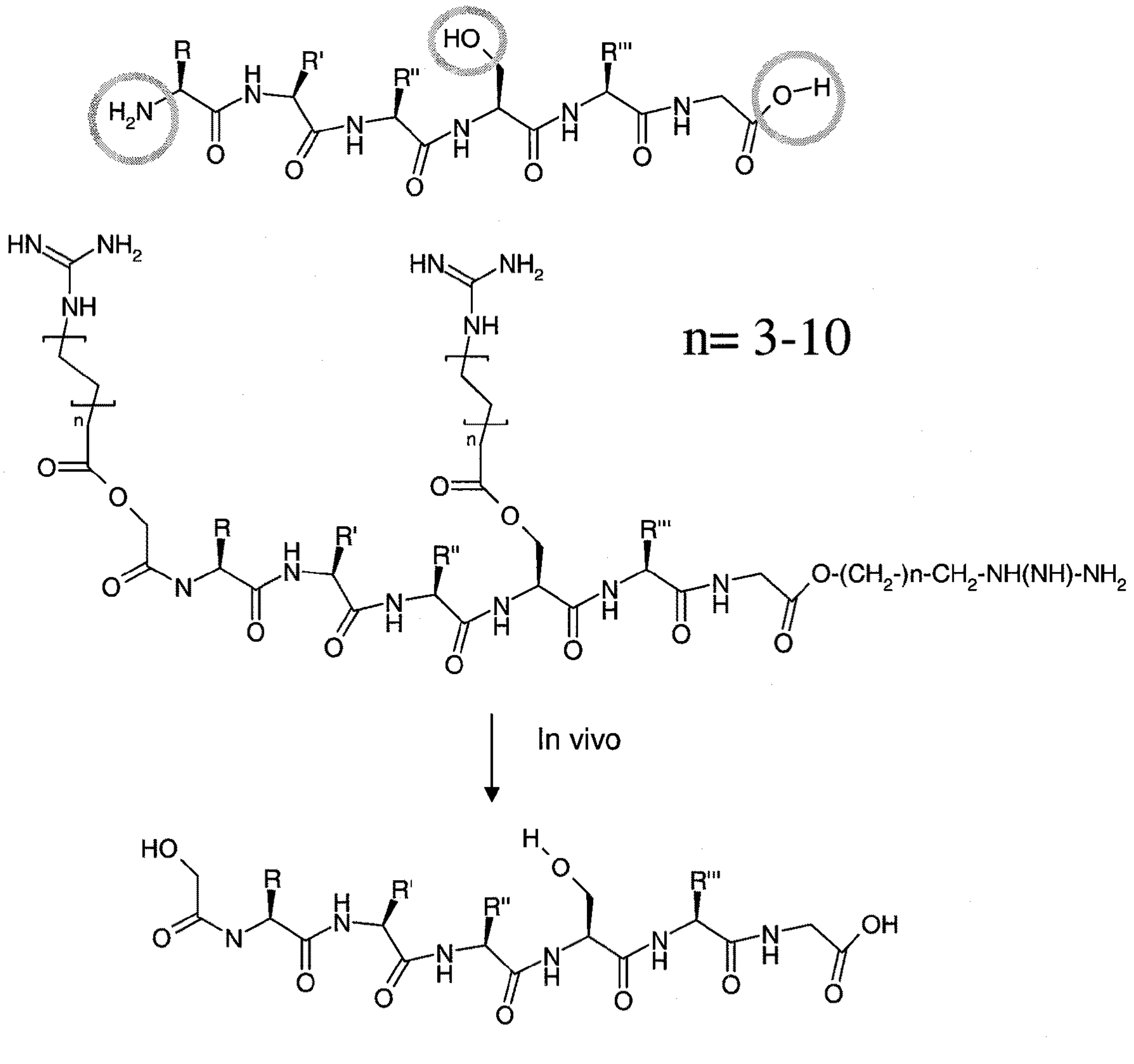

FIG. 3: Exemplary schematic drawing illustrating the modification of backbone and side chains of a peptide.

Figure 4:
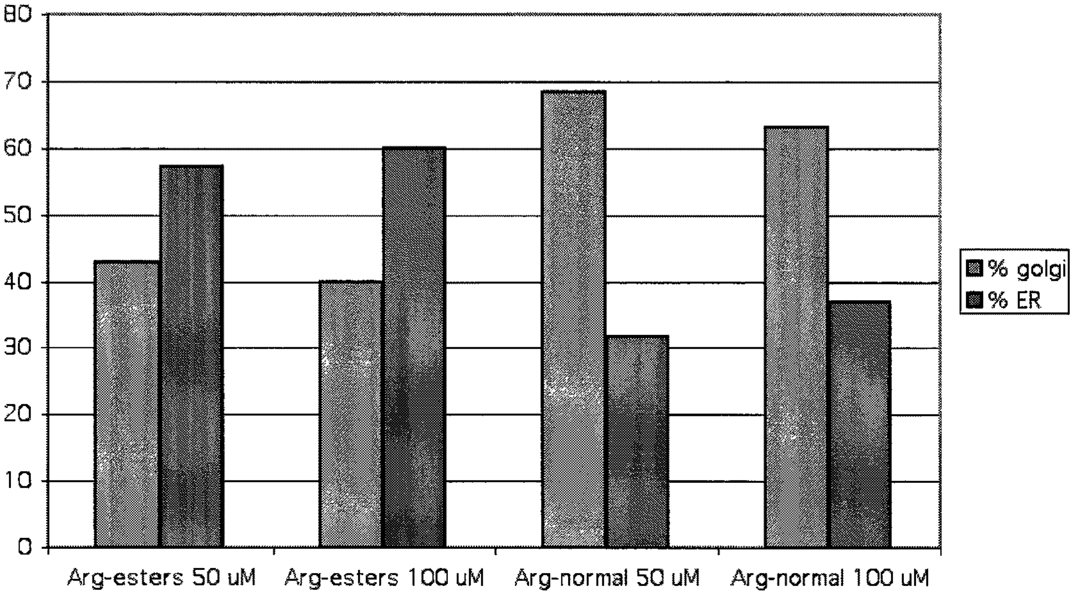

FIG. 4: Arginine-ester modified peptides block export of a SCF-reporter construct to the endoplasmatic reticulum. Y-axis: % of cells exhibiting Golgi-staining (blue) of reporter construct: 2-hours pretreatment and 1-hour ER-to Golgi transport. Arg-normal peptide is comparable to ER-to Golgi transport of non-treated cells.

Figure 5:
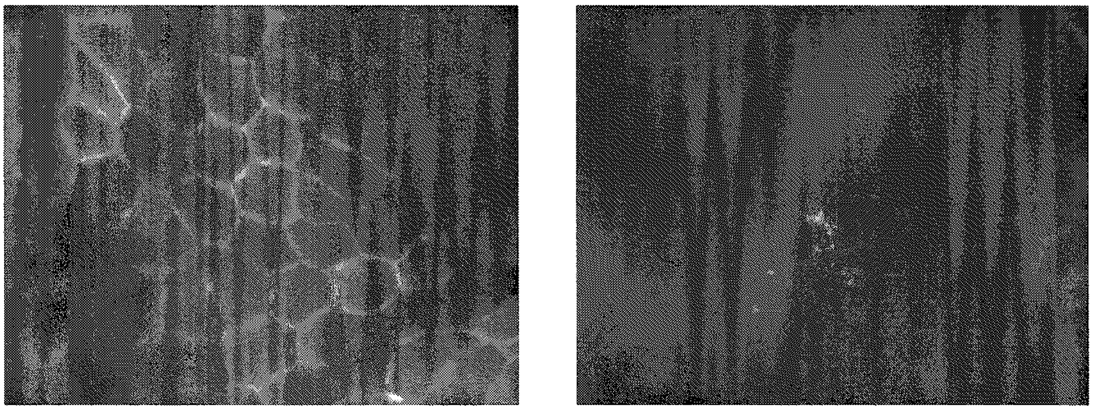

FIG. 5: Arginine-ester peptide delivery and inhibition of SCF transport to the cell surface (16 hours). Left: No peptide; normal SCF membrane staining. Right: Arginine-ester peptide (100 μM); shift to intracellular SCF staining.

FIG. 6: Example of a nucleic acid of the invention. The shown nucleic acid may be part of a longer nucleic acid by forming phospho-diester bonds at the free 5'- and 3'-hydroxyl groups.

FIG. 7: In vivo phosphate ester cleavage mechanism by initial disulfide reduction followed by intramolecular cleavage.

Figure 8:
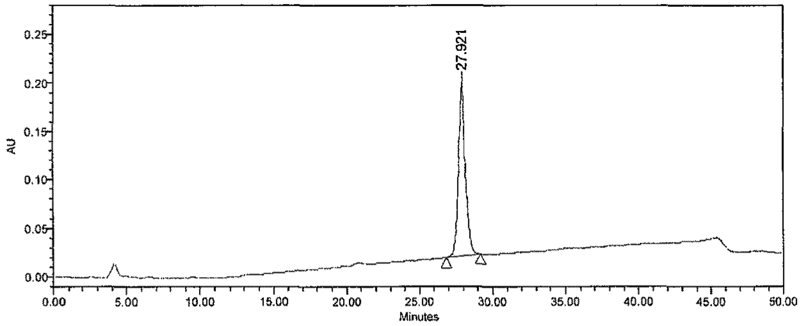

FIG. 8: HPLC chromatogram of the peptide of Example 1.

Figure 9:
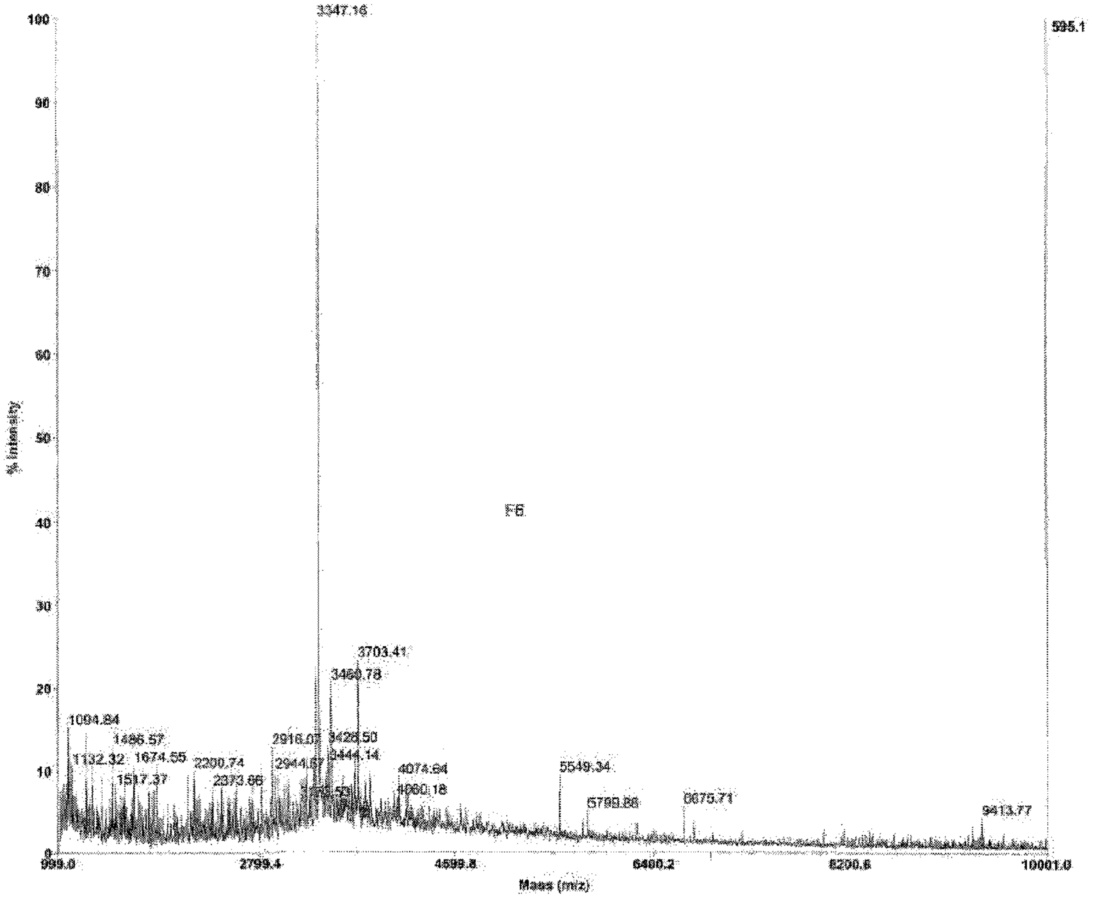

FIG. 9: Mass spectrum of the peptide of Example 1.

The following examples illustrate the invention but should not be construed as being limiting.

EXAMPLE 1

Delivery the of 20-mer Peptide Inhibitor of SCF (Stem Cell Factor) without Using Fusogenic (i.e. Cell-Penetrating) Peptides Target-Peptide (Required for ER-Export of SCF):
-N-E-E-D-N-E-I-S-M-L-Q-E-K-E-R-E-F-Q-E-V-cooH (SEQ. ID NO: 1)

Corresponding arginine-ester-peptide, i.e., the peptide is modified according to the invention by esterifying the carboxylates of glutamates with a guanidinium alkanol:

```
Gnd  Gnd   Gnd       Gnd     Gnd Gnd     Gnd
  \  /     /           \     /   /       /
N-E-E-D-N-E-I-S-M-L-Q-E-K-E-R-E-F-Q-E-V-COOH
```

Gnd=Guanidinium Group

The aspartic acid side chain was protected with a methyl ester: Boc-Asp(OMe)-OH

I. Pseudoarginine-Derived-SFC Derivatives:

The guanidinium group was chemically incorporated into glutamic acid side chains via an ester bond, separated from the carboxylic acid by an alkyl chain of 4 carbons (butyl). The Guanidinium protecting group is the Bis-Z (N,N' bis benzyloxycarbonyl).

Strategy: Boc/Fmoc strategy.

Precursor used: Fmoc-Glu(ObutylGuanidiniumBisZ)—OH.

Resin: Boc-Val-Pam resin RAPP polymer. 0.59 mmol/g. 0.2 mmol scale synthesis.

Coupling agents: BOP for precursor and HCTU for the rest.

Solid phase peptide synthesis was accomplished using manual coupling. TFA cleavage was short (1×1 minute) to avoid BisZ cleavage. Fmoc groups were removed using the standard 20% piperidine cycle. Finally, HF cleavage was performed. Purity and identity of the product was confirmed by HPLC (see FIG. 8) and MS-Maldi-TOF (Expected M+H=3346, found 3347; see FIG. 9).

II. Synthesis of Precursors:
Fmoc-Glu(OBisZGuanidiniumbutyl)-OH
Starting material: Fmoc-Glu-OtBu Fmoc-Glu-OtBu → (Bis-Z-guanidiniumhydroxylbutyl; DCC, HOBt, DMAP, DMF) Fmoc-Glu(ObutylguanidiniumBisZ)-OtBu → (TFA) Fmoc-Glu(ObutylguanidiniumBisZ)-OH Experimental Protocol:

Cos-7 cells were plated overnight on glass coverslips in 10% serum containing DMEM. For the analysis, we suspended the peptide at 1 mM in PBS (phosphate buffered saline) which was diluted to final concentration in full medium. We washed the cells after 15 or 30 minutes and washed once with PBS and fixed with paraformaldehyed (4%) for 10 minutes and took images in PBS.

To improve the strategy, (i) a longer carbon spacer was used to avoid possible side reactions (lactam formation), and (ii) all Boc chemistry was used to simplify the chain assembly. In this case one starts with 6-amino-1-hexanol to obtain an amino acid ready for Boc solid phase peptide synthesis:

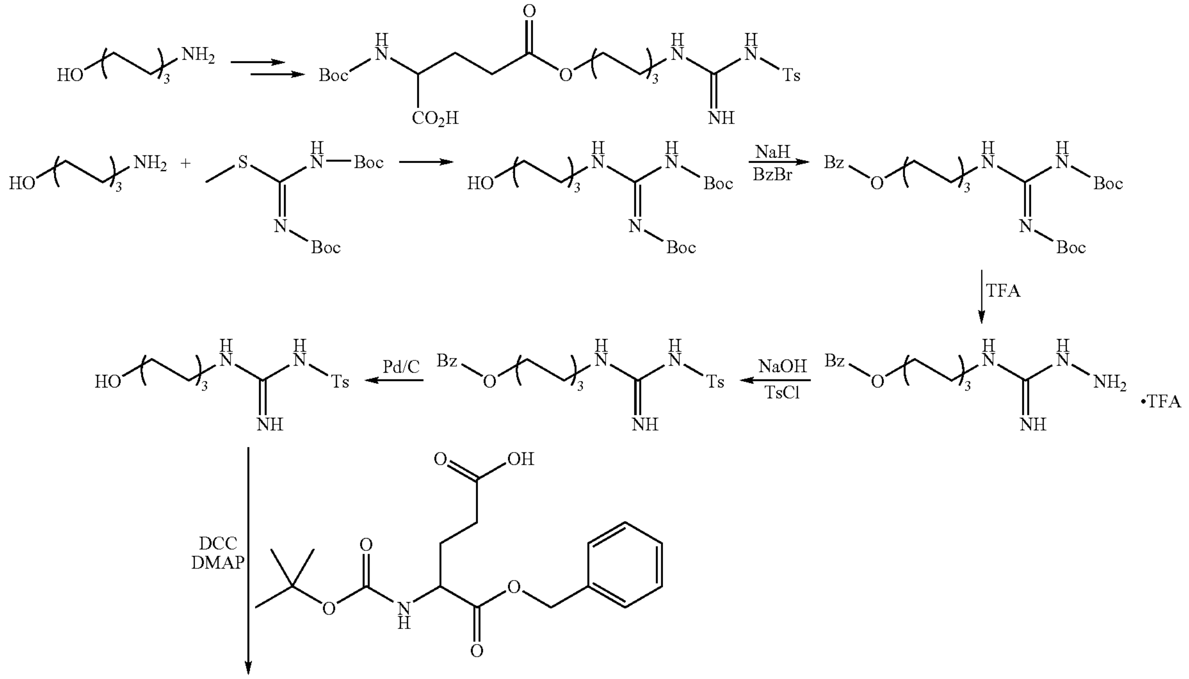

-continued

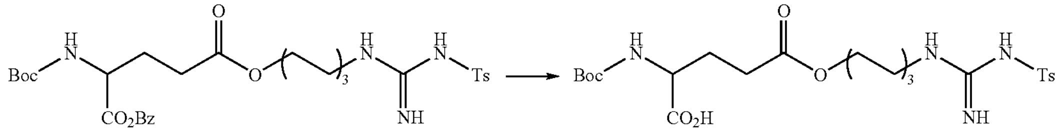

EXAMPLE 2

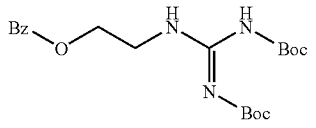

Synthesis of 1-(2-(benzyloxy)Ethyl)-N,N'-di-Boc-guanidine 49.9 mg (1 mmol, 1 eq.) of NaH were suspended under nitrogen in 10 mL of dry THF. A solution of 298.3 mg (1 mmol, 1 eq.) of 1-(6-hydroxyethyl)-N,N'-di-Boc-guanidine in 10 mL of dry THF were added dropwise in $10^{min}$. The solution was stirred at room temperature for $1^{hour}$ and 0.12 mL (1 mmol, 1 eq.) of benzyl bromide were added dropwise. The reaction was stirred for $2^{h}30^{min}$ at room temperature and checked by TLC. 44.9 mg (1 mmol, 1 eq.) of NaH were added. After 5 h30 min (total reaction time), the TLC shows little advancement and the reaction was allowed to stir overnight. Some water was added and the organic solvent was removed in vacuo. The aqueous phase was extracted 3 times with ether. The organic phase was dried over anhydrous $Na_2SO_4$ and evaporated to give 430.0 mg of a colorless oil. This oil was purified by flash chromatography over silica (eluant AcOEt: pentane 1:9; $R_f$=0.26) to obtain 315.5 mg (0.8 mmol) of 1-(2-(benzyloxy)ethyl)-N,N'-di-Boc-guanidine as a colorless oil (yield=80%).

EXAMPLE 3

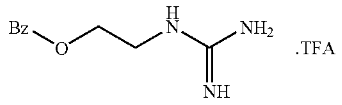

Synthesis of 2-guanidinoethyl benzoate triflate salt 4 mL (52 mmol, 65 eq.) of TFA were added to 315.5 mg (0.8 mmol, 1 eq.) of 1-(2-(benzyloxy)ethyl)-N,N'-di-Boc-guanidine and stirred at room temperature for 3 hours. The solution was evaporated to give 336.9 mg (1.1 mmol) of 2-guanidinoethyl benzoate triflate salt as a slightly orange oil (yield=110%).

EXAMPLE 4

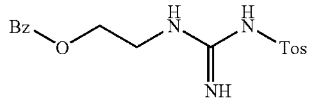

Synthesis of N—(N-(2-(benzyloxy)ethyl)carbamimidoyl)-4-methylbenzenesulfonamide 164.5 mg (0.4 mmol, 1 eq.) of 2-guanidinoethyl benzoate triflate salt were dissolved in some acetone. 4 mL of a 4 M NaOH solution were added. 86.1 mg (0.44 mmol, 1.1 eq.) of toluene-4-sulfonyl-chloride were dissolved in acetone and added to the reaction mixture. The reaction was stirred 2 hours at room temperature and the reaction was neutralized with a 6M HCl solution. Acetone was removed in vacuo. The aqueous phase was extracted 3 times with AcOEt. The organic phase dried over anhydrous $Na_2SO_4$ and evaporated to give 174.8 mg of a colorless oil. The formation of white crystals happened over week end. These crystals were washed with AcOEt to remove the surrounding oil. 83.8 mg (0.24 mmol) of N—(N-(2-(benzyloxy)ethyl)carbamimidoyl)-4-methylbenzenesulfonamide were recovered as white crystals (yield=60%).

EXAMPLE 5

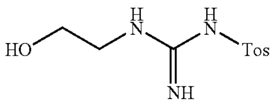

Synthesis of N—(N-(2-hydroxyethyl)carbamimidoyl)-4-methylbenzenesulfonamide 83.8 mg (0.24 mmol) of N—(N-(2-(benzyloxy)ethyl)carbamimidoyl)-4-methylbenzenesulfonamide were dissolved under nitrogen in MeOH. A few mg of 10% Palladium over activated charcoal were added. 3 vacuo hydrogen flush were done before stirring vigorously the reaction under a $H_2$ atmosphere. After 2 hours, no conversion was found by TLC (eluant AcOEt:pentane 9:1) and approximatively 5 times the amount of starting Palladium over activated charcoal was added. The rection was stirred overnight. The TLC showed the formation of a more polar product unless the reaction was far from being complete. 1 mL of acetic acid was added. One hour after the reaction was complete. The reaction was filtered over celite and the solvent evaporated to afford 62.8 mg (0.24 mmol) of N—(N-(2-hydroxyethyl)carbamimidoyl)-4-methylbenzenesulfonamide as a white solid (yield=100%).

EXAMPLE 6

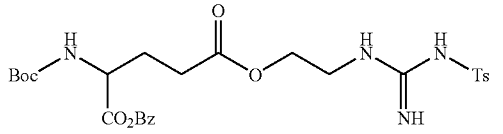

Synthesis of benzoic 1-imino-13,13-dimethyl-1-(4-methylphenylsulfonamido)-6,11-dioxo-5,12-dioxa-2,10-diazatetradecane-9-carboxylic anhydride 62.8 mg (0.24 mmol, 1 eq.) of N—(N-(2-hydroxyethyl) carbamimidoyl)-4-methylbenzenesulfonamide and 82.7 mg (0.24 mmol, 1 eq.) of Boc-L-glutamic acid 1-benzyl ester were dissolved under nitrogen in dry dichloromethane. 7.45 mg (0.05 mmol, 0.2 eq.) of DMAP and 55.3 mg (0.26 mmol, 1 eq.) of DCC were added. The reaction was stirred overnight at room temperature. A white precipitate appeared and was removed by filtration. The solvent was evaporated in vacuo to afford 184.1 mg of a white solid. This white solid was dissolved in dichloromethane and purified by preparative TLC (eluant pure AcOEt, Rf=0.65). 83.2 mg (0.14 mmol) of benzoic 1-imino-13,13-dimethyl-1-(4-methylphenylsulfonamido)-6,11-dioxo-5,12-dioxa-2,10-diazatetradecane-9-carboxylic anhydride were recovered as a colorless oil (yield=60%). $^1$H-NMR (500 MHz, $CDCl_3$): δ=1.12 (m, 1H), 1.41 (s, 9H), 1.86 (m, 1H), 2.18 (m, 1H), 2.39 (m, 5H), 3.41 (m, 1H), 3.61 (m, 1H), 4.01 (m, 1H), 4.26 (m, 1H), 4.35 (m, 1H), 5.17 (q, J=11.98 Hz, 2H), 5.33 (d, J=8.83 Hz, 1H), 6.49 (m, 2H), 7.22 (d, J=8.20 Hz, 2H), 7.34 (m, 5H), 7.77 (d, J=8.19 Hz, 2H).

EXAMPLE 7

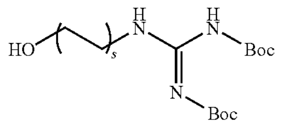

Synthesis of 1-(6-hydroxyhexyl)-N,N'-di-Boc-guanidine 7.255 g (24.99 mmol, 1 eq.) of 1,3-di-Boc-2-methyl-isothiourea, 4.101 g (34.98 mmol, 1.4 eq.) of 6-amino-1-hexanol and 614.5 mg (5 mmol, 0.2 eq.) of DMAP were dissolved in 140 mL of dichloromethane. The reaction was stirred at room temperature and followed by TLC (eluant AcOEt:pentane 3:7). After approximately 60 hours, the reaction was complete. Solvent was evaporated in vacuo (under the hood and bubbling the gaz in a NaOCl solution, evaporation of MeSH). The oil obtained was dissolved in dichloromethane (white flakes still present) and washed 3 times with a 1M $KHSO_4$ solution and 1 time with brine. The organic phase was dried over anhydrous $Na_2SO_4$ and the solvent was evaporated in vacuo to give 10.43 g of a colorless oil. This oil was purified by flash chromatography over silica (eluant AcOEt:pentane 1:1; $R_f$=0.43) to give 8.447 g (23.50 mmol) of 1-(6-hydroxyhexyl)-N,N'-di-Boc-guanidine as a colorless oil (yield=94%) which became a white solid overnight. $^1$H-NMR (500 MHz, $CDCl_3$): δ=1.42 (m, 5H), 1.52 (s, 10H), 1.53 (s, 10H), 1.58 (t, J=6.94 Hz, 2H), 1.64 (m, 2H), 3.61 (m, 2H), 3.65 (t, J=6.64 Hz, 2H).

EXAMPLE 8

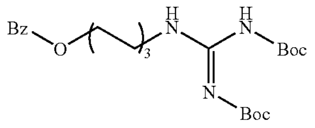

Synthesis of 1-(2-(benzyloxy)hexyl)-N,N'-di-Boc-guanidine 1.300 g (32.49 mmol, 1.3 eq.) of sodium hydride were suspended under nitrogen in 170 mL of dry THF. 8.983 g (24.99 mmol, 1 eq.) of 1-(6-hydroxyhexyl)-N,N'-di-Boc-guanidine dissolved in dry THF were added dropwise to the suspension. The reaction was stirred at room temperature for $45^{min}$. 3.6 mL (29.99 mmol, 1.2 eq.) of benzyl bromide were added dropwise in $10^{min}$. The reaction was stirred overnight at room temperature. The reaction was checked by TLC and the reaction wasn't complete. 0.833 g (20.82 mmol) of sodium hydride were added. After 1 hour, the TLC was the same and 0.810 g (20.24 mmol) of sodium hydride were added. After 3 hours, no evolution was seen on TLC, 1.396 g (34.89 mmol) of sodium hydride and 1.6 mL (13.33 mmol) of benzyl bromide were added. The reaction was stirred overnight and TLC was still the same. The reaction was quenched by addition of water until clear solution. THF was removed in vacuo. Aqueous phase was extracted 3 times with ether. Organic phase was dried over anhydrous $Na_2SO_4$ and evaporated to obtain 15.44 g of a slightly yellow oil. This oil was purified by flash chromatography over silica (eluant AcOEt:pentane 1:9; $R_f$=0.43) to obtain 3.78 g of 1-(2-(benzyloxy)hexyl)-N,N'-di-Boc-guanidine as a colorless oil (yield=34%). $^1$H-NMR (500 MHz, $CDCl_3$): δ=1.39 (m, 5H), 1.50 (s, 9H), 1.51 (s, 9H), 1.61 (m, 5H), 3.45 (m, 4H), 4.50 (m, 2H), 7.28 (m, 1H), 7.34 (m, 4H).

EXAMPLE 9

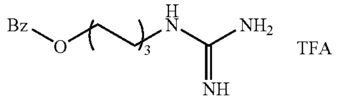

Synthesis of 2-guanidinohexyl benzoate triflate salt 4.61 g (10.3 mmol, 1 eq.) of 1-(2-(benzyloxy)hexyl)-N,N'-di-Boc-guanidine were dissolved in 49 mL (669 mmol, 65 eq.) of TFA. The reaction was stirred for 3 hours at room temperature. The TFA was removed in vacuo to afford 6.06 g of a brown oil (yield=162%).

EXAMPLE 10

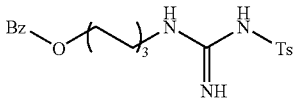

Synthesis of N—(N-(6-(benzyloxy)hexyl)carbamimidoyl)-4-methylbenzenesulfonamide 6.06 g (10.3 mmol, 1 eq.) of crude 2-guanidinohexyl benzoate triflate salt were dissolved in acetone and 50 mL of a 4 M NaOH solution were added. 2.377 g (12.4 mmol, 1.2 eq.) of toluene-4-sulfonyl-chloride were dissolved in acetone and added to the reaction mixture. As a brown oil was present over the solution, acetone was added until complete dissolution. The reaction was stirred overnight at room temperature. Reaction was neutralized (pH=6 to litmus) by adding a 37% HCl solution. Acetone was removed in vacuo and the aqueous phase was extracted 3 times with AcOEt. The organic phase was dried over anhydrous $Na_2SO_4$ and solvent was evaporated to afford 5.23 g of a slightly yellow oil. This oil was purified by flash chromatography over silica (eluant AcOEt: pentane 6:4; $R_f$=0.52) to afford 3.20 g (7.9 mmol) of N—(N-(6-(benzyloxy)hexyl)carbamimidoyl)-4-methylbenzenesulfonamide as a colorless oil (yield=77%). $^1$H-NMR (500 MHz, $CDCl_3$): $\delta$ =1.27 (m, 5H), 1.44 (m, 2H), 1.55 (m, 2H), 2.38 (s, 3H), 3.11 (s, 2H), 3.44 (t, J=6.62 Hz, 3H), 4.48 (s, 2H), 6.30 (s, 3H), 7.22 (d, J=8.20, 2H), 7.28 (m, 1H), 7.33 (m, 2H), 7.73 (d, J=8.19 Hz, 2H).

EXAMPLE 11

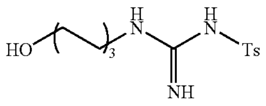

Synthesis of N—(N-(6-hydroxyhexyl)carbamimidoyl)-4-methylbenzenesulfonamide 3.20 g (7.9 mmol) of N—(N-(6-(benzyloxy)hexyl)carbamimidoyl)-4-methylbenzenesulfonamide were dissolved under nitrogen in MeOH. A few mg of 10% Palladium over activated charcoal were added. 1 mL of acetic acid was added. 3 vacuo hydrogen flush were done before stirring vigorously the reaction under a $H_2$ atmosphere. The reaction was vigorously stirred at room temperature for 3 hours and checked by TLC. No conversion was found and 2 mL of acetic acid were added. After 1 hour, the TLC showed no conversion and more 10% Palladium over activated charcoal were added. After 3 days, the TLC showed a complete conversion and the solution was filtered over celite and the solvent evaporated to afford 2.480 g of N—(N-(6-hydroxyhexyl)carbamimidoyl)-4-methylbenzenesulfonamide as slightly yellow oil was obtained (yield=100%).

EXAMPLE 12

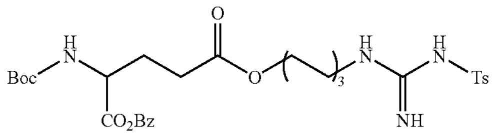

Synthesis of 1-benzyl 5-(6-(3-tosylguanidino)hexyl) 2-(tert-butoxycarbonylamino)pentanedioate 2.48 g (7.9 mmol, 1 eq.) of N—(N-(6-hydroxyhexyl)carbamimidoyl)-4-methylbenzenesulfonamide and 2.67 g (7.9 mmol, 1 eq.) of Boc-L-glutamic acid 1-benzyl ester were dissolved under nitrogen in dry dichloromethane. 198.9 mg (1.58 mmol, 0.2 eq.) of DMAP and 1.810 g (8.7 mmol, 1.1 eq.) of DCC were added at room temperature. The reaction was stirred overnight and a white precipitate appeared. The precipitate was removed by filtration and the solvent evaporated to afford 5.99 g of a mixed yellow oil/solid compound. This compound was purified by flash chromatography over silica (eluant pure AcOEt; $R_f$=0.71) to afford 4.83 g of a slightly yellow oil (yield=97%).

EXAMPLE 13

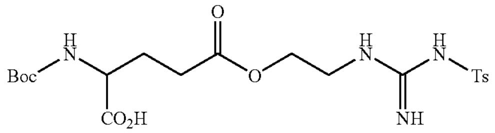 [SMILES: Cc1ccc(S(=O)(=O)NC(=N)NCCOC(=O)CCC(NC(=O)OC(C)(C)C)C(=O)O)cc1]

Synthesis of 1-imino-17,17-dimethyl-1-(4-methylphenylsulfonamido)-10,15-dioxo-9,16dioxa-2,14-diazaoctadecane-13-carboxylic acid 103.6 mg (0.16 mmol) of 1-benzyl 5-(6-(3-tosylguanidino)hexyl) 2-(tert-butoxycarbonylamino)pentanedioate under nitrogen in MeOH. A few mg of 10% Palladium over activated charcoal were added. 3 vacuo hydrogen flush were done before stirring vigorously the reaction under a $H_2$ atmosphere for 2 days. The reaction was filtered over celite and the solvent evaporated to give 74.4 mg of a colorless oil (yield=86%).

The invention claimed is:

1. A nucleic acid (a) which is esterified at one or more phosphates with a guanidinium alkanol or a PEG substituted with a guanidinium group and having a free hydroxyl group;

wherein the guanidinium alkanol has a structure of:

$$HO—(CR_1R_2)_n—N(R_3)—C(═NR_4)—NHR_5 \quad \text{(Formula I)}$$

wherein the PEG substituted with a guanidinium group and having a free hydroxyl group has a structure of:

$$HO—(CH_2CH_2(OCH_2CH_2)_k—N(R_3)—C(═NR_4)—NHR_5 \quad \text{(Formula V)}$$

wherein:

n is an integer from 2 to 15;

k is an integer from 1 to 12;

each occurrence of $R_1$ and $R_2$ is independently selected from H; halogen; $NH_2$; alkyl with 1 to 5 carbon atoms;

$R_3$ is H or alkyl with 1 to 5 carbon atoms; and $R_4$ and $R_5$ are each independently selected from H; alkyl with 1 to 5 carbon atoms; aryl;

heteroaryl, wherein the N bearing the $R_4$ or $R_5$ group may be a ring atom of the heteroaryl; and/or a heteroaryl ring formed by $R_4$ and $R_5$.

2. The nucleic acid of claim 1, wherein one or more terminal phosphates, if not esterified with a guanidinium alkanol, are esterified with a fatty alcohol.

3. The nucleic acid of claim 1, wherein the nucleic acid is selected from the group consisting of DNA, RNA, and siRNA.

4. A pharmaceutical composition comprising a nucleic acid of claim 1.

5. A pharmaceutical composition comprising a nucleic acid active agent having at least one: phosphate esterified with a compound comprising a single guanidinium group, wherein:

i. the nucleic acid active agent comprises at least one phosphate esterified with a compound comprising a single guanidinium group, wherein the compound comprising the single guanidinium group is selected from the group consisting of a guanidinium alkanol, and a PEG substituted with a guanidinium group and having a free hydroxyl; or ii. the nucleic acid active agent comprises at least one phosphate esterified with a compound comprising a single guanidinium group, and wherein the compound comprising the single guanidinium group includes a sulfhydryl group forming a disulfide with a sulfhydryl group of a linker joined to the phosphate as an ester; or iii. the nucleic acid active agent comprises at least one backbone hydroxyl converted into an acetal with a compound comprising a single guanidinium group, wherein the compound comprising the single guanidinium group is selected from the group consisting of a guanidinium alkanol, and a PEG substituted with a guanidinium group.

6. The pharmaceutical composition of claim 5, wherein the nucleic acid active agent comprises at least one terminal or backbone hydroxyl esterified with a compound comprising a single guanidinium group, wherein the compound comprising the single guanidinium group is selected from the group consisting of a guanidinium alkanoic acid, and a PEG substituted with a guanidinium group and a carboxyl group.

7. The pharmaceutical composition of claim 5, wherein the nucleic acid active agent comprises at least one phosphate esterified with a compound comprising a single guanidinium group, wherein the compound comprising the single guanidinium group is selected from the group consisting of a guanidinium alkanol, and a PEG substituted with a guanidinium group and having a free hydroxyl.

8. The pharmaceutical composition of claim 5, wherein the nucleic acid active agent comprises at least one phosphate esterified with a compound comprising a single guanidinium group, and wherein the compound comprising the single guanidinium group includes a sulfhydryl group forming a disulfide with a sulfhydryl group of a linker joined to the phosphate as an ester.

9. The pharmaceutical composition of claim 8, wherein the compound comprising a single guanidinium including a sulfhydryl is selected from the group consisting of a guanidinium alkanethiol, and a PEG substituted with a guanidinium group and a sulfhydryl group.

10. The pharmaceutical composition of claim 5, wherein the nucleic acid active agent comprises at least one backbone hydroxyl converted into an acetal with a compound comprising a single guanidinium group, wherein the compound comprising the single guanidinium group is selected from the group consisting of a guanidinium alkanol, and a PEG substituted with a guanidinium group.

11. The pharmaceutical composition of claim 5, wherein the nucleic acid active agent comprises from 4 to 20 guanidinium groups.

12. The pharmaceutical composition of claim 5, wherein the nucleic acid active agent is selected from the group consisting of DNA, RNA, and siRNA.

13. The nucleic acid of claim 1, wherein the guanidinium alkanol has a structure of:

$$HO—(CH_2)_n—N(R_3)—C(═NH)—NH_2 \quad \text{(Formula II)}$$

wherein:

n is an integer from 2 to 10; and $R_3$ is H or alkyl with 1 to 5 carbon atoms.

* * * * *

SEQUENCE LISTING

<160> NUMBER OF SEQ ID NOS: 1

<210> SEQ ID NO 1
<211> LENGTH: 20
<212> TYPE: PRT
<213> ORGANISM: Homo sapiens

<400> SEQUENCE: 1

-continued

```
Asn Glu Glu Asp Asn Glu Ile Ser Met Leu Gln Glu Lys Glu Arg Glu
1               5                   10                  15

Phe Gln Glu Val
            20
```